US009282881B2

(12) United States Patent
Singh et al.

(10) Patent No.: US 9,282,881 B2
(45) Date of Patent: Mar. 15, 2016

(54) 3D IMAGE SHOOTING APPARATUS AND ENDOSCOPE

(75) Inventors: Brahm Pal Singh, Osaka (JP); Katsuhiro Kanamori, Nara (JP); Masao Hiramoto, Osaka (JP)

(73) Assignee: Panasonic Intellectual Property Management Co., Ltd., Osaka (JP)

(*) Notice: Subject to any disclaimer, the term of this patent is extended or adjusted under 35 U.S.C. 154(b) by 737 days.

(21) Appl. No.: 13/571,998

(22) Filed: Aug. 10, 2012

(65) Prior Publication Data
US 2012/0300033 A1  Nov. 29, 2012

Related U.S. Application Data

(63) Continuation of application No. PCT/JP2012/000001, filed on Jan. 4, 2012.

(30) Foreign Application Priority Data

Feb. 1, 2011  (JP) .................................. 2011-020084

(51) Int. Cl.
*A61B 1/045* (2006.01)
*A61B 1/00* (2006.01)
(Continued)

(52) U.S. Cl.
CPC ............. *A61B 1/045* (2013.01); *A61B 1/00193* (2013.01); *G03B 15/05* (2013.01);
(Continued)

(58) Field of Classification Search
CPC .... A61B 1/00193; A61B 1/045; G03B 15/05; G03B 35/02; H04N 13/0048; H04N 13/0217; H04N 13/0253; H04N 2005/2255

USPC ........................................................... 348/45
See application file for complete search history.

(56) References Cited

U.S. PATENT DOCUMENTS 5,424,535 A * 6/1995 Albion et al. ................. 250/225
5,649,897 A   7/1997 Nakamura et al.
(Continued)

FOREIGN PATENT DOCUMENTS

CN  1870932 A  11/2006
JP  09-090241 A  4/1997
(Continued)

OTHER PUBLICATIONS

Chinese Search report for corresponding Chinese Application No. 201280002286.6 (with English Translation) dated Apr. 3, 2015.
(Continued)

*Primary Examiner* — Anner Holder
(74) *Attorney, Agent, or Firm* — Renner, Otto, Boisselle & Sklar, LLP

(57) ABSTRACT

An exemplary 3D image shooting apparatus comprises: a polarized light source; an image capturing section that sequentially captures an image of the object that is being illuminated with each of plane polarized light rays, and an image processor. The image capturing section includes: a lens; an image sensor; and an incoming light transmitting section which has a transparent area and a plurality of polarization filter areas. The polarization filter areas are arranged outside of the transparent area, generally have a concentric ring shape, and include left and right filter areas so that their polarization transmission axis directions define an angle $\alpha$ ($0<\alpha<90$ degrees). The image processing section generates a plurality of images from light that has been transmitted through the transparent area and light that has been transmitted through the plurality of polarization filter areas.

6 Claims, 19 Drawing Sheets

(51) Int. Cl.
  *G03B 15/05* (2006.01)
  *G03B 35/02* (2006.01)
  *H04N 13/00* (2006.01)
  *H04N 13/02* (2006.01)
  *H04N 5/225* (2006.01)

(52) U.S. Cl.
  CPC .......... *G03B 35/02* (2013.01); *H04N 13/0048* (2013.01); *H04N 13/0217* (2013.01); *H04N 13/0253* (2013.01); *G03B 2215/05* (2013.01); *H04N 2005/2255* (2013.01)

(56) References Cited

U.S. PATENT DOCUMENTS

| | | | |
|---|---|---|---|
| 6,807,295 B1* | 10/2004 | Ono | 382/154 |
| 2001/0031912 A1* | 10/2001 | Adler | 600/109 |
| 2003/0083551 A1 | 5/2003 | Takahashi | |
| 2005/0020926 A1 | 1/2005 | Wiklof et al. | |
| 2009/0079982 A1 | 3/2009 | Lefaudeux | |
| 2009/0166517 A1* | 7/2009 | Moribe | G01N 21/956 250/225 |
| 2009/0244339 A1 | 10/2009 | Murooka et al. | |
| 2010/0102211 A1* | 4/2010 | Murooka | A61B 1/0638 250/226 |
| 2010/0311005 A1* | 12/2010 | Liang | A61B 1/00009 433/29 |
| 2012/0105598 A1 | 5/2012 | Hiramoto et al. | |

FOREIGN PATENT DOCUMENTS

| | | |
|---|---|---|
| JP | 11-313242 A | 11/1999 |
| JP | 2001-016611 A | 1/2001 |
| JP | 2003-098570 A | 4/2003 |
| JP | 2003-222804 A | 8/2003 |
| JP | 2010-104424 A | 5/2010 |
| JP | 2011/142062 A1 | 11/2011 |
| WO | 2011/142062 A1 | 11/2011 |

OTHER PUBLICATIONS

International Search Report for corresponding International Application No. PCT/JP2012/000001 mailed Mar. 13, 2012.

Form PCT/ISA/237 for corresponding International Application No. PCT/JP2012/000001 mailed Mar. 13, 2012.

Lefaudeux et al., "Compact and robust linear Stokes polarization camera", Proc. SPIE, vol. 6972, 69720B, Polarization: Measurement, Analysis, and Remote Sensing VIII (2008).

Green et al., "Multi-Aperture Photography", ACM Transactions on Graphics, vol. 26, No. 3, Article 68, Jul. 2007.

Co-pending U.S. Appl. No. 13/255,386, filed Sep. 8, 2011.
Co-pending U.S. Appl. No. 13/255,393, filed Sep. 8, 2011.
Co-pending U.S. Appl. No. 13/498,940, filed Mar. 29, 2012.
Co-pending U.S. Appl. No. 13/498,598, filed Mar. 28, 2012.

* cited by examiner (b)

(a)

TRANSPARENT AREA C

POLARIZATION FILTER AREA L    POLARIZATION FILTER AREA R

POLARIZATION FILTER AREA L
TRANSPARENT AREA C
POLARIZATION FILTER AREA R

PLANE POLARIZED LIGHT TO RADIATE

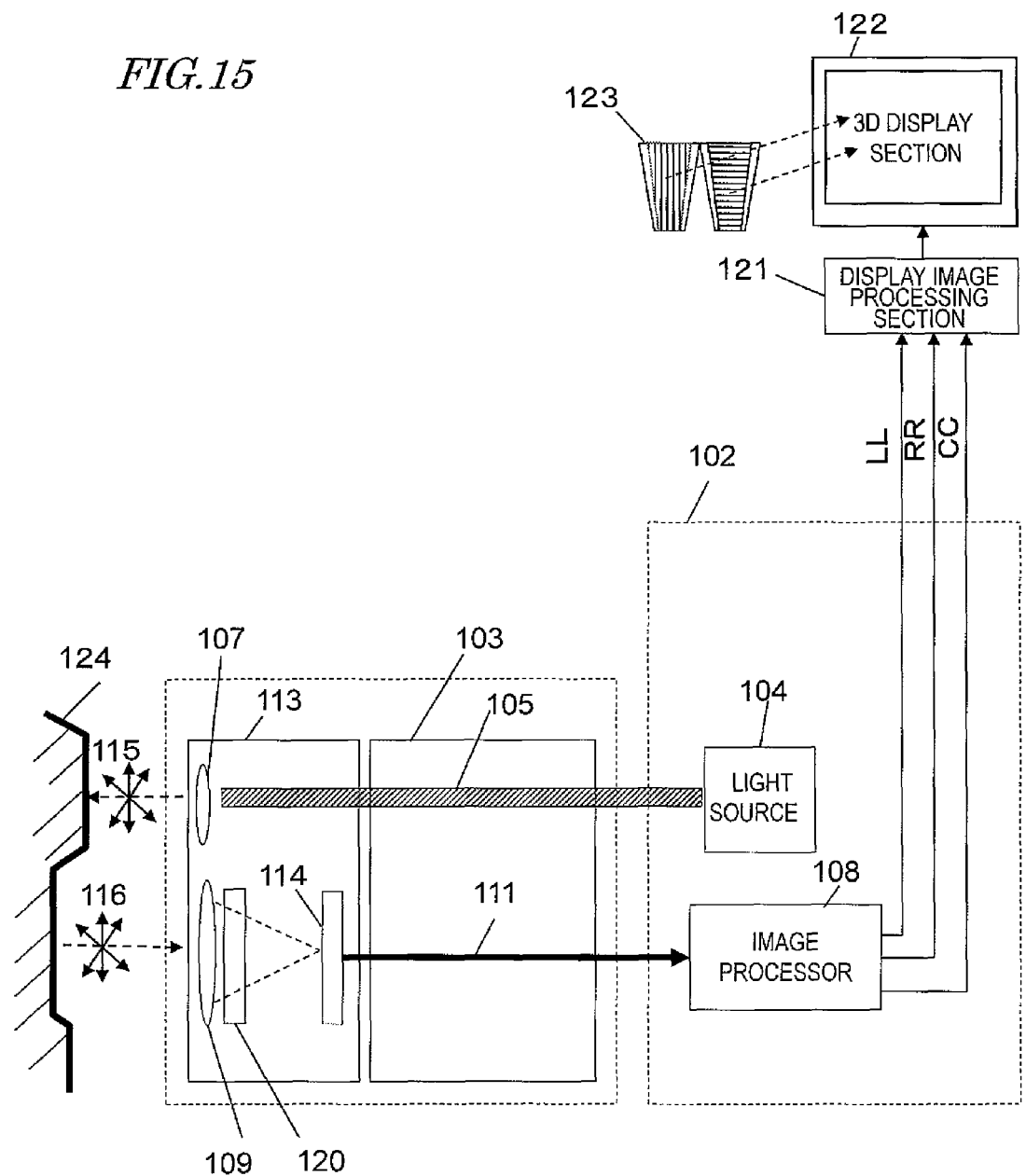

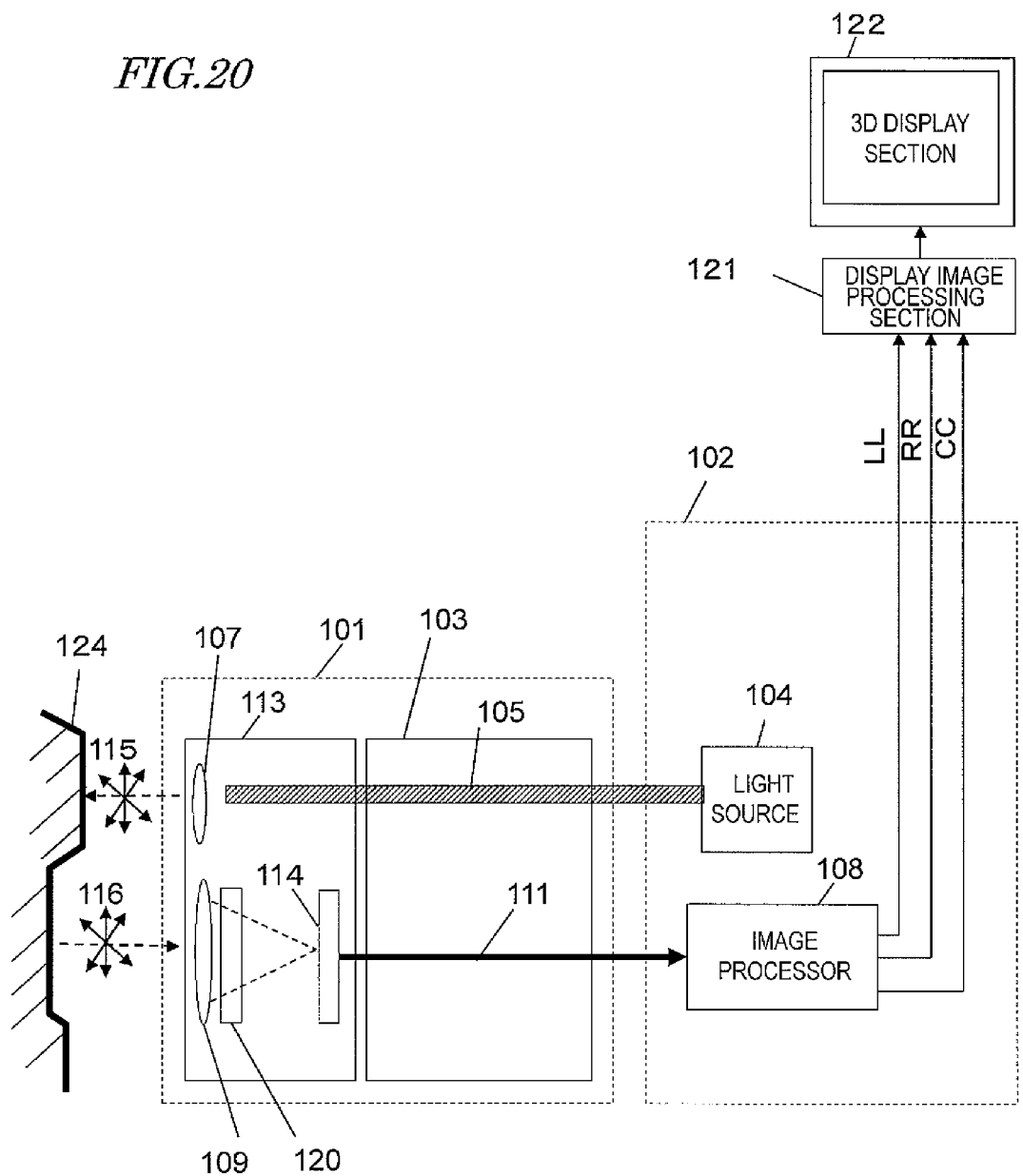

POLARIZATION FILTER AREA

TRANSPARENT AREA

3D IMAGE SHOOTING APPARATUS AND ENDOSCOPE

This is a continuation of International Application. No. PCT/JP2012/000001, with an international filing date of Jan. 4, 2012, which claims priority of Japanese Patent Application No. 2011-020084, filed on Feb. 1, 2011, the contents of which are hereby incorporated by reference.

BACKGROUND

1. Technical Field

The present disclosure relates to a 3D image shooting apparatus and endoscope.

2. Description of the Related Art

An endoscope captures an image of an organism's organ by irradiating the entire wall surface of the organ, which is covered with a mucosa, with illuminating light. In the field of such endoscopes, in order to observe the 3D shape of the wall surface of the organ, it is important to extract information about the depth of the object. Meanwhile, in the field of surgical endoscopes, the region in surgery should be monitored three-dimensionally. To meet these demands, technologies for three-dimensional (3D) endoscopes have been developed. A 3D endoscope ordinarily adopts a "stereo vision system" that uses two lens-image sensor sets to obtain multi-viewpoint images by viewing the object from multiple different points. Such a stereo vision system can obtain a pair of multi-viewpoint images with parallax (which may be a left-eye image and a right-eye image, for example) from the same object at the same time, and therefore, can get information about the 3D shape of the object based on the multi-viewpoint images. However, it is difficult for a stereo vision system to perfectly match the characteristics of its two image sensors to each other, which is a problem with such a system. Thus, to avoid such a problem, a technology for a "single vision system" that uses only one lens-image sensor set to obtain multi-viewpoint images as disclosed in Japanese Laid-Open Patent Publication No. 2001-16611 has attracted a lot of attention these days.

SUMMARY

The prior art technique needs further improvement in view of the effective use of the incoming light.

One non-limiting, and exemplary embodiment provides a practical 3D image shooting apparatus and endoscope that can obtain 3D information about the shape (micro-geometry or topography) of an object's surface.

In one general aspect, a 3D image shooting apparatus includes: a polarized light source section that sequentially illuminates an object with three or more kinds of plane polarized light rays, of which the planes of polarization define mutually different angles; an image capturing section that sequentially captures an image of the object that is being illuminated with each of the plane polarized light rays; and an image processing section. The image capturing section includes: a lens that produces an image of light that has returned from the object that is being illuminated by the polarized light source section; an image sensor that generates, through photoelectric conversion, a pixel signal based on the image produced by the lens; and an incoming light transmitting section which transmits the light that has returned from the object and which has a transparent area and a plurality of polarization filter areas. The plurality of polarization filter areas are arranged outside of the transparent area, generally have a concentric ring shape, and include left and right filter areas that are respectively arranged on the left- and right-hand sides of the optical axis of the lens so that their polarization transmission axis directions define an angle α that is greater than zero degrees but smaller than 90 degrees. Based on the pixel signal that is generated by the image sensor when the object is being illuminated with each of the plane polarized light rays, the image processing section generates a plurality of images from light that has been transmitted through the transparent area and light that has been transmitted through the plurality of polarization filter areas.

In one general aspect, an endoscope includes: a polarized light source section that sequentially illuminates an object with three or more kinds of plane polarized light rays, of which the planes of polarization define mutually different angles; and an image capturing section that sequentially captures an image of the object that is being illuminated with each of the plane polarized light rays. The image capturing section includes: a lens that produces an image of light that has returned from the object that is being illuminated by the polarized light source section; an image sensor that generates, through photoelectric conversion, a pixel signal based on the image produced by the lens; and an incoming light transmitting section which transmits the light that has returned from the object and which has a transparent area and a plurality of polarization filter areas. The plurality of polarization filter areas are arranged outside of the transparent area, generally have a concentric ring shape, and include left and right filter areas that are respectively arranged on the left- and right-hand sides of the optical axis of the lens so that their polarization transmission axis directions define an angle α that is greater than zero degrees but smaller than 90 degrees.

According to the above aspect, it is possible to improve the sensitivity of a 3D image capturing.

These general and specific aspects may be implemented using a system, a method, and a computer program, and any combination of systems, methods, and computer programs.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

BRIEF DESCRIPTION OF THE DRAWINGS

FIG. 15 illustrates a configuration for a 3D image shooting apparatus as a second embodiment of the present invention.

FIG. 20 illustrates a configuration for a 3D image shooting apparatus as a fourth embodiment of the present invention.

DETAILED DESCRIPTION

Embodiment 1

Figure 1:
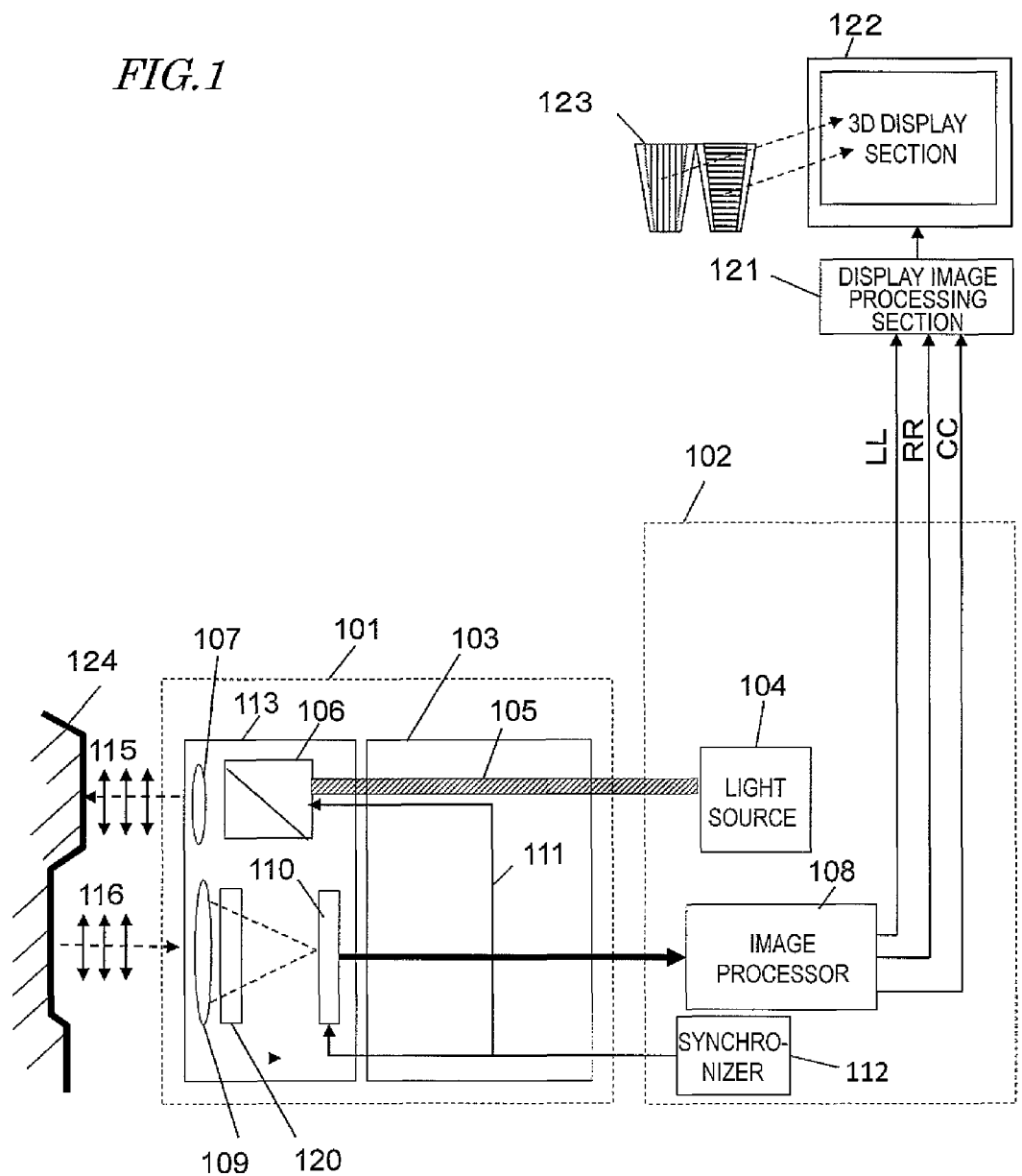
FIG. 1 illustrates a configuration for a 3D image shooting apparatus as a first embodiment of the present invention.

FIG. 1 schematically illustrates an overall configuration for a 3D image shooting apparatus as a first embodiment of the present disclosure. This 3D image shooting apparatus includes an endoscope 101 and a controller 102. The endoscope 101 includes a tip portion 113 with an image sensor 110 and an inserting portion 103 with a light guide 105 and a video signal line 111. The inserting portion 103 actually has a structure that is more elongated horizontally than shown in FIG. 1 and that can be bent flexibly. Even when bent, the light guide 105 can also propagate light.

The controller 102 includes a light source 104, an image processor 108 and a synchronizer 112. An image signal is output from the controller 102 to a 3D display section 122 by way of a display image processing section 121. The image that has been output to the 3D display section 122 is monitored by a physician, for example, using a pair of viewing glasses 123.

Figure 2:
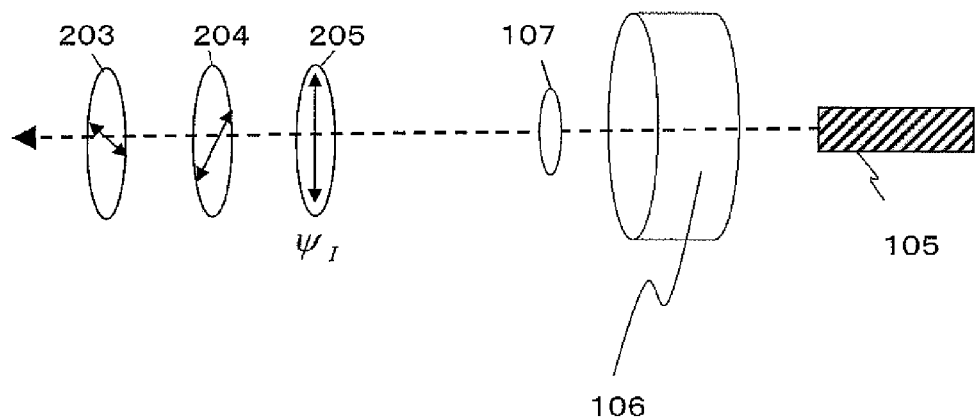
FIG. 2 shows how a plane of polarization control element operates.

The white non-polarized light that has been emitted from the light source 104 is guided through the light guide 105 to a plane of polarization control element 106 of the tip portion 113. FIG. 2 illustrates an arrangement for the plane of polarization control element 106.

The plane of polarization control element 106 is a device that can rotate the plane of polarization using a liquid crystal material. Its exemplary configurations are already disclosed in Japanese Laid-Open Patent Publication No. 11-313242, United States Laid-Open Patent Publication No. 2009/0079982, and Nicolas Lefaudeux et al.: "Compact and Robust Linear Stokes Polarization Camera", Proc. SPIE, Vol. 6972, 69720B, Polarization: Measurement, Analysis, and Remote Sensing VIII (2008). The plane of polarization control element 106 may be implemented as a voltage application type liquid crystal device that includes a ferroelectric liquid crystal material, a polarization film and a quarter-wave plate in combination. The plane of polarization control element 106 transforms the non-polarized light that has been produced by the light source 104 and then transmitted through the light guide 105 into plane polarized light that has a plane of polarization at an arbitrary angle of polarization. In FIG. 1, the polarization direction 115 of the light with which the object is irradiated and the polarization direction 116 of the light that has returned from the object are schematically indicated. Since the polarization direction is held even after the light has been reflected from the object as will be described later, the polarization directions 115 and 116 agree with each other.

The synchronizer 112 gives the plane of polarization control element 106 an instruction to rotate the plane of polarization, thereby getting the plane of polarization of the illumination rotated. And that polarized illumination is cast toward the object through an illuminating lens 107. At the same time, the synchronizer 112 sends a shooting start signal to an image sensor 110, thereby getting video. The synchronizer 112 performs this series of processing steps a number of times.

The image capturing system of this embodiment captures first, second and third images in respective states 203, 204, and 205 in which the plane of polarization has an angle of 0, 45, and 90 degrees, respectively. It is not always necessary to use these three angles for the planes of polarization. But the angles of the planes of polarization may also be defined arbitrarily. If the image sensor has high sensitivity or if the illumination has high illuminance, then the exposure process time can be shortened. As a result, the angle of rotation can be set more finely.

According to the documents described above, the time it takes to rotate the plane of polarization may be as long as approximately 20 ms when the operating speed is low but may also be as short as 40 to 100 μsec when the operating speed is high. If a high-response-speed liquid crystal material is used and if the sensitivity of the image sensor is increased to a level that is high enough to get an image captured in such a short time, performance that is high enough to shoot a moving picture can be maintained even when the plane of polarization is rotated to those three directions one after another during shooting. Also, this image processing is performed on images to be captured on an at least three frame basis. However, the actual processing time can also be within one frame period by adopting pipeline processing.

The light returning from the object is transmitted through the shooting lens 109, passes through an incoming light transmitting section 120, and then produces an image on the image sensor 110. The configuration and function of the incoming light transmitting section 120 will be described later. This image sensor 110 may be either a monochrome image sensor or a single-panel color image sensor with a color mosaic. The video signal of the captured image is transmitted through the video signal line 111 to reach the image processor 108.

The image processor 108 performs image processing on multiple images that have been captured, thereby generating an image CC, a left viewpoint image LL and a right viewpoint image RR. These images are processed by the display image processing section 121 and then displayed on the 3D image display section 122. The image displayed on the 3D image display section 122 can be observed as a 3D image through a pair of viewing glasses 123. As this 3D image display section 122, an ordinary 3D display device that displays left and right viewpoint images may be used.

Figure 3:
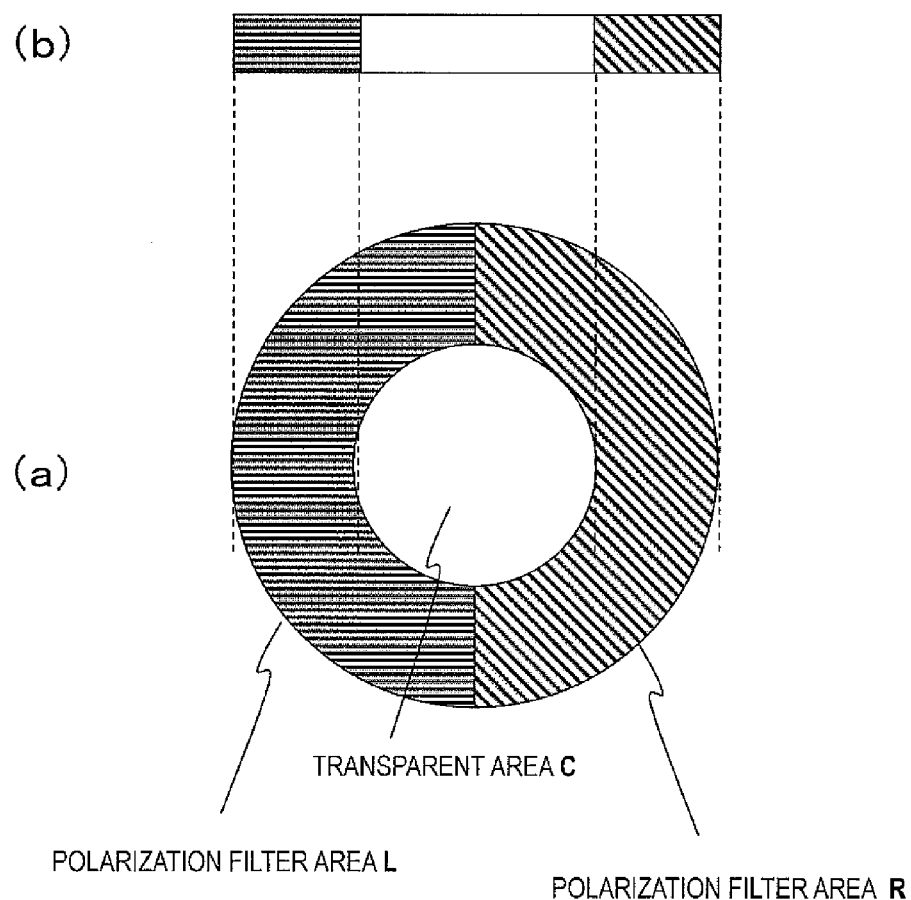
FIG. 3 is respectively a plan view and cross-sectional view illustrating the structure of an incoming light transmitting section.

FIG. 3 illustrates the incoming light transmitting section 120. Specifically, portion (a) of FIG. 3 is a plan view of the incoming light transmitting section 120 as viewed from the image sensor 110, while portion (b) of FIG. 3 illustrates a cross section of the incoming light transmitting section 120. As shown in portion (a) of FIG. 3, the incoming light transmitting section 120 is comprised of an optically transparent area C and left and right polarization filter areas L and R, each of which has a polarization filter. These polarization filter areas L and R generally have a concentric ring shape and surround the transparent area C. The center of the concentric ring polarization filter areas (L+R) agrees with the center of the transparent area C. The polarization filter areas L and R are a left-hand-side filter and a right-hand-side filter that are respectively arranged on the left- and right-hand sides of the optical axis of the lens. In this description, if two areas are arranged on the left- and right-hand sides, it means that those areas are arranged symmetrically to each other with respect to a virtual reference plane including the optical axis of the lens. Since the direction and orientation of the tip portion 113 of the endoscope 101 will change during shooting, those "up and down" and "right and left" directions are just relative ones.

A certain angular difference α (where 0<α<90 degrees) is defined between the respective transmission axes of the polarization filters that are provided for the left and right filter areas L and R as viewed from the image sensor 110.

In the example illustrated in FIG. 1, the incoming light transmitting section 120 is arranged between the shooting lens 109 and the image sensor 110. However, the incoming light transmitting section 120 does not always have to be arranged at that position but may also be arranged between the object and the shooting lens 109. Alternatively, the incoming light transmitting section 120 may even form an integral part of the shooting lens 120, too.

The incoming light transmitting section 120 typically includes a transparent substrate, which may be a glass plate, for example, and a pair of polarization filters that are attached to predetermined areas of the transparent substrate. In that case, the rest of the transparent substrate, to which no polarization filters are attached, functions as the transparent area C. In another example, the incoming light transmitting section 120 may be comprised of a pair of polarization filters and a member that holds the polarization filters. In that case, the transparent area C may be the air. The planar area of the transparent area C may account for 10 to 50% of the overall planar area of the polarization filter areas L and R and the transparent area C.

According to the present disclosure, as the object is illuminated with a polarized light source, the light that has returned from the subject is also polarized. Part of the returning light is transmitted through the transparent area C of the incoming light transmitting section 120 and another part of the returning light is transmitted through one of the two polarization filter areas L and R.

Figure 4A:
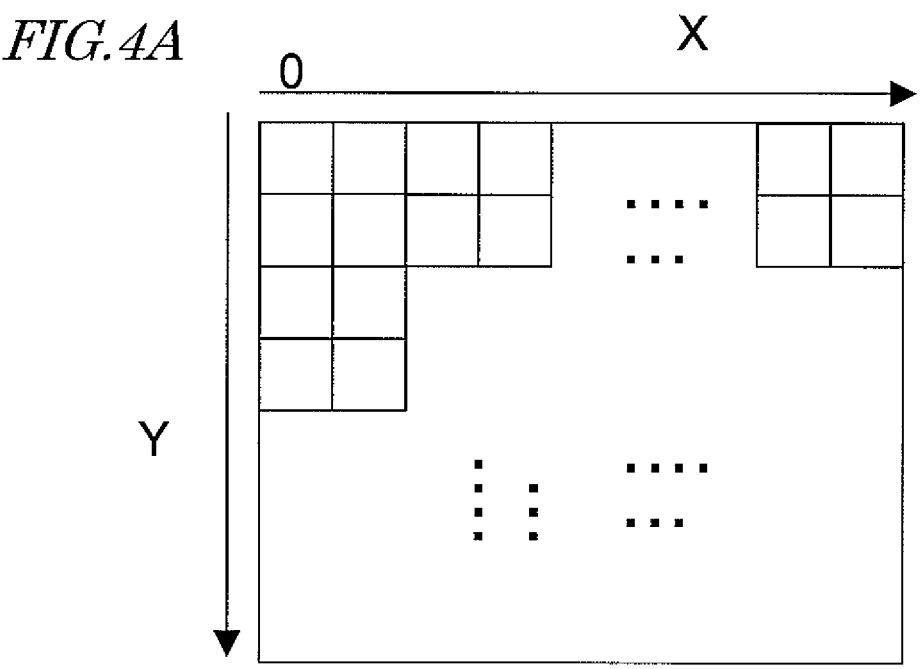
FIGS. 4A and 4B illustrate an exemplary arrangement of photosensitive cells in an image sensor.
Figure 4B:
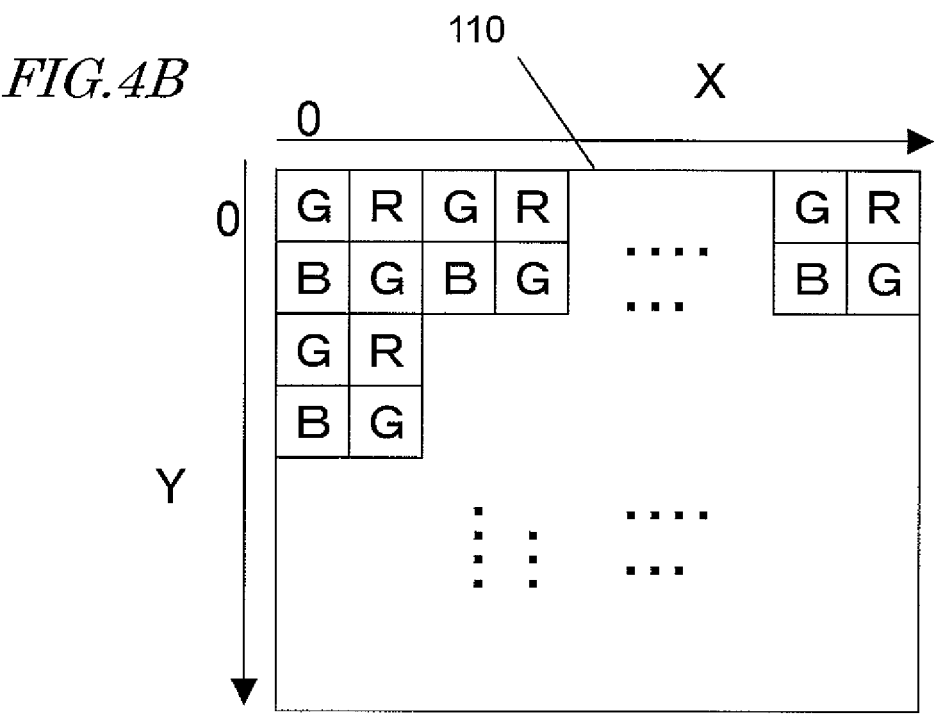

FIGS. 4A and 4B illustrate an exemplary arrangement for the image capturing plane of the image sensor 110. As shown in FIG. 4A, a number of photosensitive cells (i.e., photodiodes) are arranged in columns and rows (i.e., in X and Y directions) on the image capturing plane. When a color image is going to be captured, color mosaic filters, which transmit light rays with three different wavelengths associated with RGB, are arranged as shown in FIG. 4B. Each of these photosensitive cells generates, by photoelectric conversion, an electrical signal representing the quantity of the light received. This part may be the same as that of an ordinary single-panel color image sensor. Thus, a known image sensor to capture a light intensity image in colors may be used as the image sensor 110. In this embodiment, if the illumination is plane polarized light, an image is captured with its plane of polarization rotated, thereby obtaining information about the object's surface.

Figure 5:
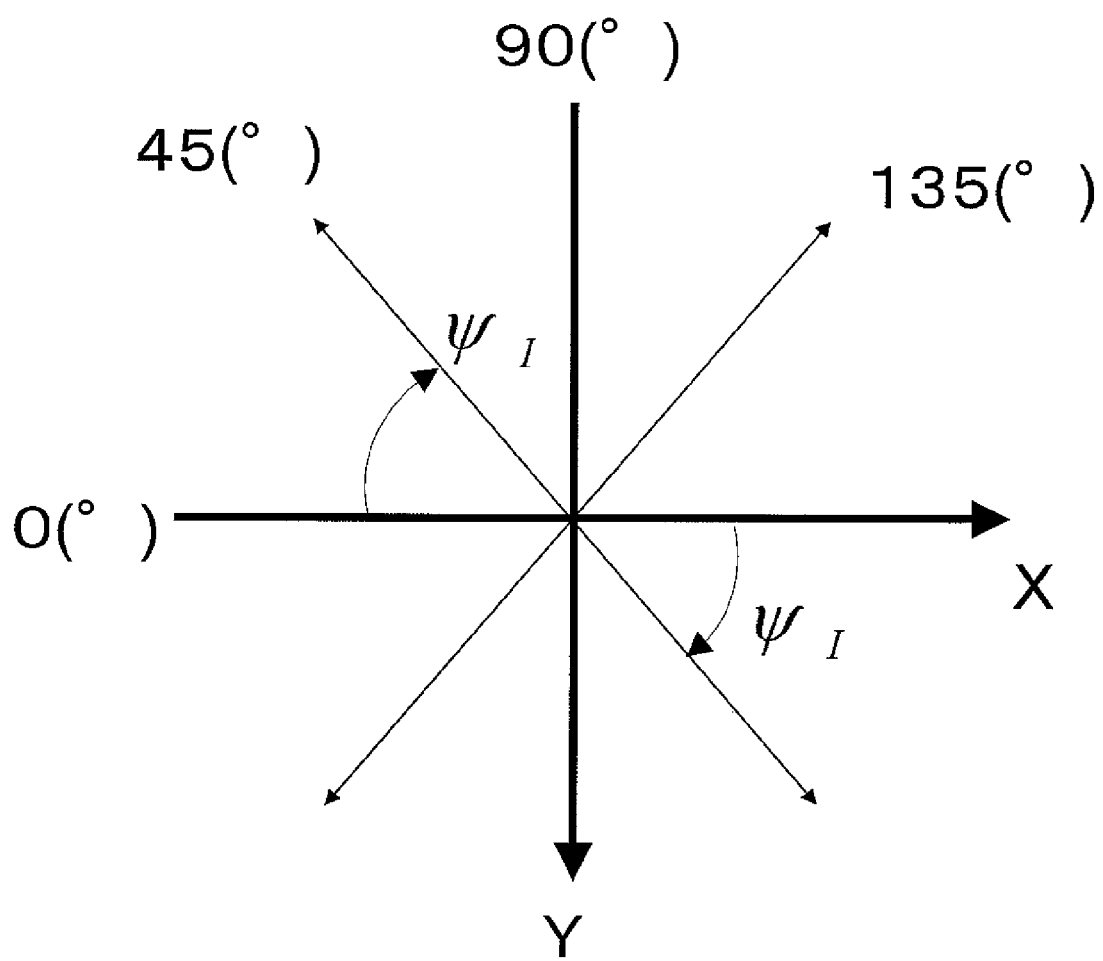
FIG. 5 shows how to define the angle of a plane of polarization.

FIG. 5 shows how the plane of polarization of polarized light source has its angle ψI defined. An X-Y coordinate system is defined as a virtual focal plane from the image sensor toward the object. In this case, the angle ψI of the plane of polarization is defined as shown in FIG. 5 with the X-axis direction set to be 0 degrees. If the angle ψI is saved for reflected light, then the respective planes of polarization of the reflected light and the incident light will have the same angle. And if the angle ψI of the plane of polarization is going to be increased or decreased, the same polarization state will recur over and over again in a period of 180 degrees. That is to say, a function that uses the angle ψI of the plane of polarization as a variable is a periodic function that has a period of 180 degrees. In this description, the angle ψI of the plane of polarization of polarized light source will be sometimes referred to herein as an "incident plane of polarization angle".

In this embodiment, the optical axis of the illuminating lens 107 is substantially aligned with that of the shooting lens 109. Such an arrangement is adopted in order to avoid casting shadows as perfectly as possible on the object being observed with an endoscope.

Generally speaking, when an endoscope is used normally, the object should be irradiated with non-polarized light in many cases. According to the present disclosure, by adding together the first, second and third polarization images described above, for example, a non-polarized light average intensity image can be generated. The results of the experiments that the present inventors carried out revealed that if images, produced by light rays that returned from object that had been irradiated with multiple polarized light rays, of which the planes of polarization angles ψI had been defined at regular intervals, were added together, the effect of the polarization was canceled and eventually the effect achieved were as if a non-polarized light source had been used.

Next, it will be described how the intensities of the light transmitted through the polarization filter areas and the transparent area of the incoming light transmitting section 120 will change if the plane of polarization of the polarized light source is rotated.

Figure 6:
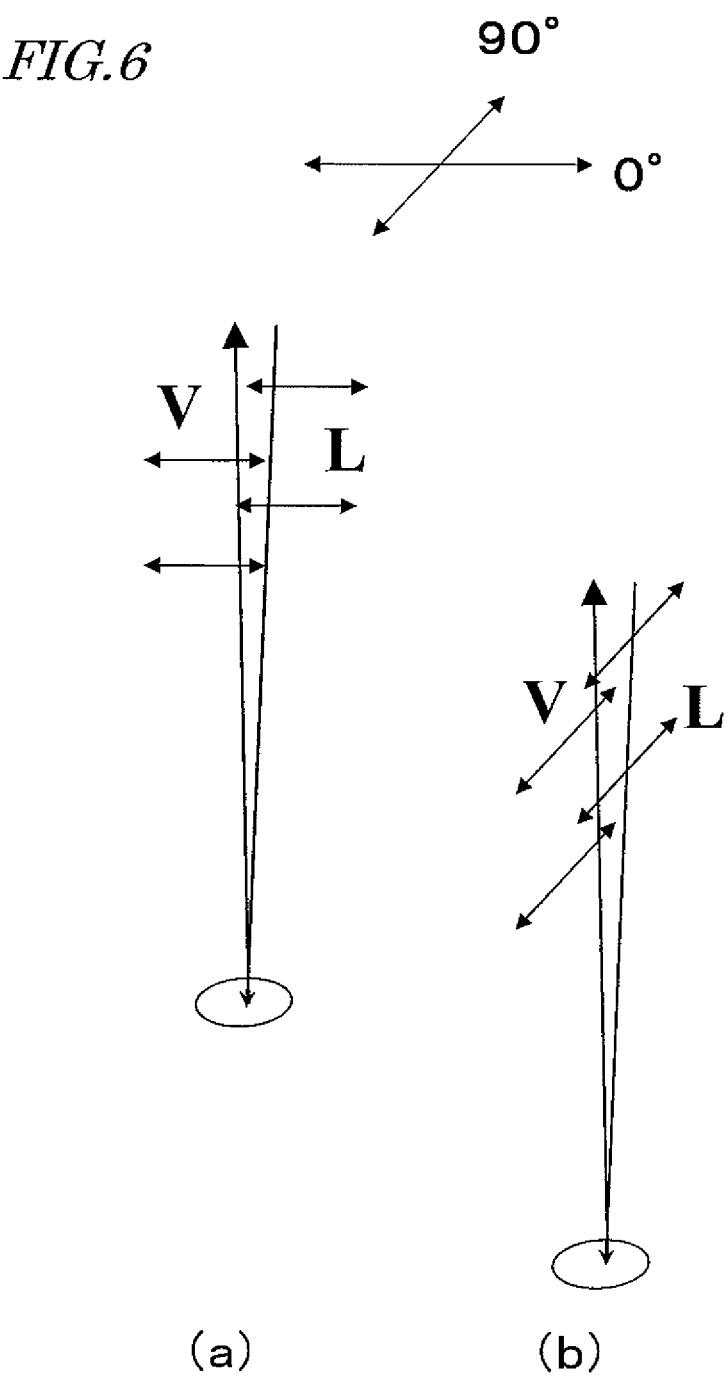
FIG. 6 illustrates how a polarized light ray that has been incident substantially perpendicularly onto a smooth and flat surface is reflected.
Figure 7:
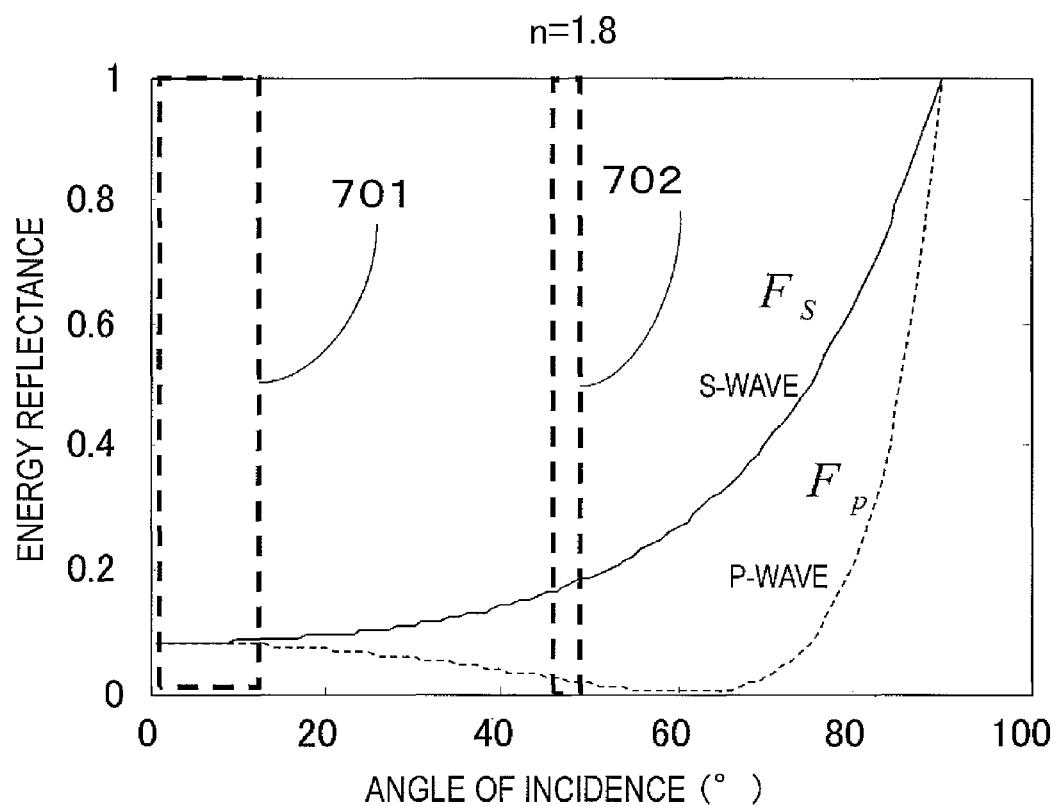
FIG. 7 shows a relation between the angle of incidence and the reflectance according to the Fresnel theory.

FIG. 6 illustrates how polarized light L is incident on a smooth and flat surface at an angle of incidence that is close to zero degrees and how its returning light V is observed with a camera. The respective angles defined by the polarization planes of the incident polarized light are different from each other by 90 degrees between portions (a) and (b) of FIG. 6. However, the plane polarization state of the returning light becomes substantially the same as that of the incoming light for the following reasons:

FIG. 7 is a graph showing the dependence of the specular reflectance according to the Fresnel theory on the angle of incidence. In FIG. 7, the abscissa represents the angle of incidence and the ordinate represents the Fresnel reflectance. These dependence curves are drawn on the supposition that the refractive index n is 1.8.

The angles of incidence of around 0 through around 15 degrees, which can be regarded as representing substantially perpendicular incidence, fall within the range 701. As can be seen from this graph, both P and S waves have substantially the same reflectance in this range 701. Therefore, if the polarized light is incident substantially perpendicularly onto the surface, then it makes almost no difference for the surface and the light is reflected in the same behavior, no matter whether the polarized light is actually a P-wave or an S-wave. This fact is satisfied extensively by any natural object with a refractive index n of 1.4 to 2.0.

As described above, if polarized light is incident on a smooth surface at an angle of incidence of almost zero degrees, reflected once and then observed, the angle ψI of the plane of polarization of the polarized light source becomes the same as the polarization angle of the returning light observed. Consequently, the ψI value of the incoming polarized light can be regarded as a known one for the observed end.

Figure 8:
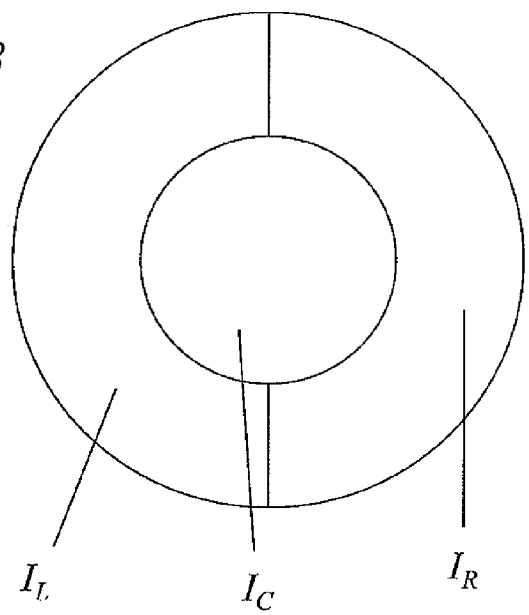
FIG. 8 illustrates a virtual state of the incoming light transmitting section without its polarization filters.

FIG. 8 schematically illustrates how the incoming light transmitting section 120 shown in FIG. 3 will look without its polarization filters. Among the light rays that form the light that has returned from a certain point on the object, the light rays transmitted through the areas L, R and C are converged by the shooting lens toward a single point on the imaging plane. In other words, the intensity I to be observed at a particular pixel on the image capturing plane is the intensity of the image, which has been produced on the image capturing plane by the light rays that have been transmitted through those areas L, R and C, at that particular pixel. Therefore, if the intensities of the light rays that have been transmitted through those areas L, R and C are identified by $I_L$, $I_R$ and $I_C$, respectively, then the intensity I to be observed at a particular pixel on the image capturing plane becomes the sum of those intensities $I_L$, $I_R$ and $I_C$:

$$I = I_L + I_R + I_C \quad (1)$$

Figure 9:
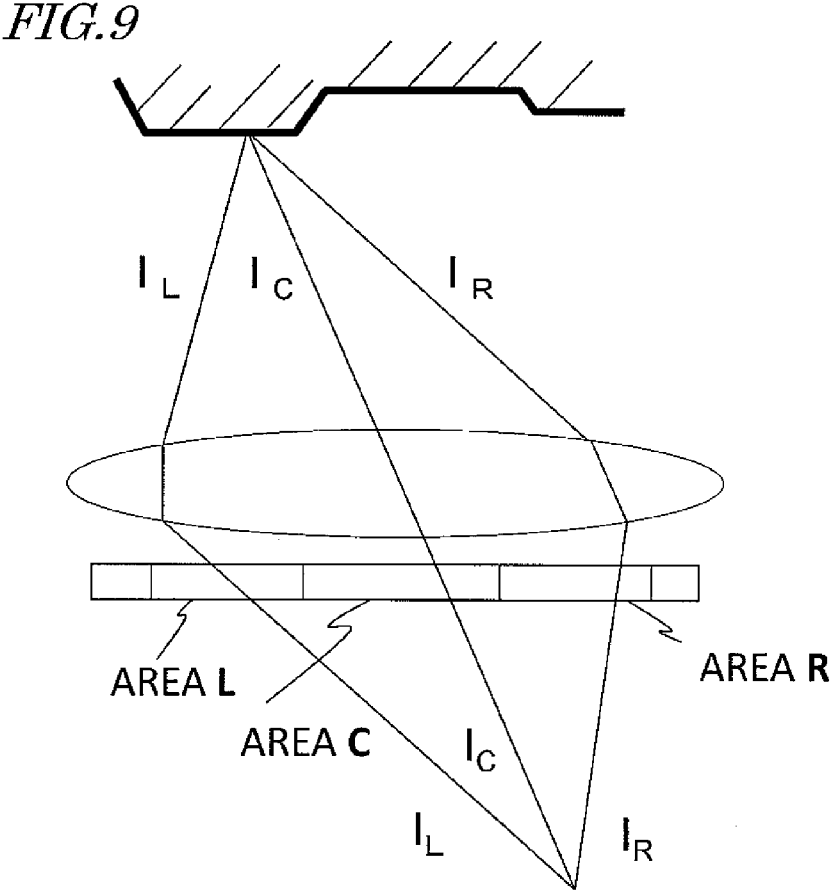
FIG. 9 illustrates how the light is transmitted through respective areas of the incoming light transmitting section with no polarization filters.

FIG. 9 schematically illustrates, with respect to a certain pixel, how the light that has returned from the object is transmitted through the areas L, C and R of the incoming light transmitting section 120 with no polarization filters. Without the polarization filters, the overall intensity of the light rays that have been transmitted through the areas L, C and R can be obtained by simply adding together the respective intensities of the light rays that have been transmitted through those three areas as represented by Equation (1). Actually, however, polarization filters that have mutually different transmission axis directions are respectively provided for the areas L and R of the incoming light transmitting section 120. That is why the quantity of the light ray transmitted through a polarization filter changes with the angle defined by the polarization direction of the incoming light (i.e., the light that has returned from the object) with respect to the transmission axis of that polarization filter. As already described with reference to FIGS. 6 and 7, the polarization direction of a light ray that has been reflected from a flat surface of an object agrees with that of the light with which the object is illuminated. Consequently, if the angle of the plane of polarization of a polarized light source is controlled, then the plane of polarization of the light incident on the incoming light transmitting section 120 (i.e., the light that has returned from the object) can be adjusted.

Figure 10A:
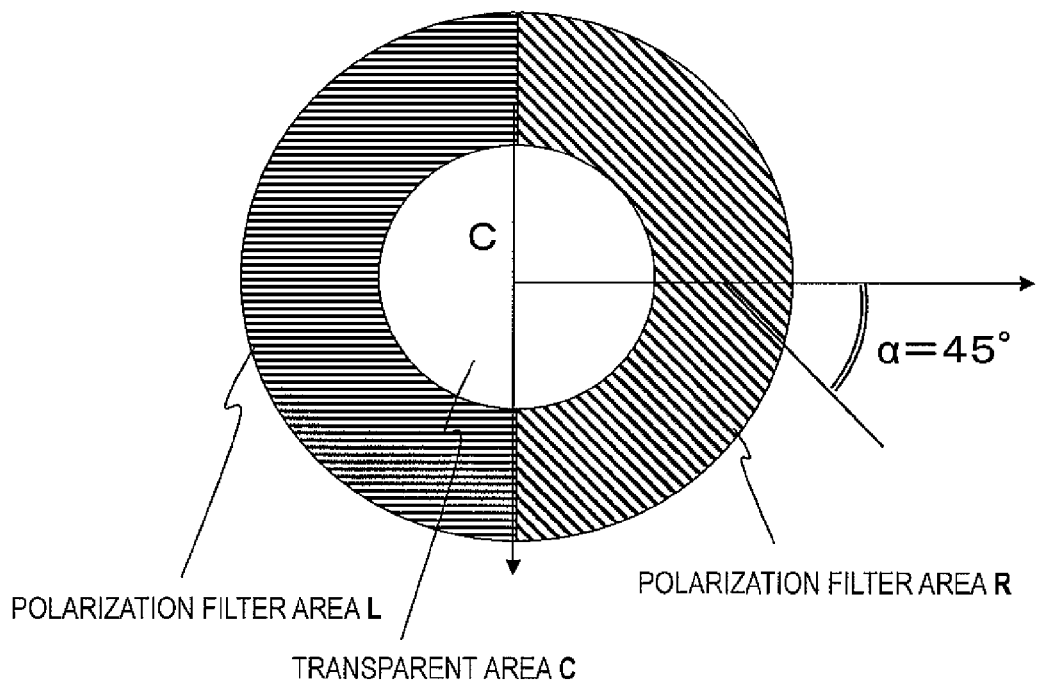
FIG. 10A is a plan view illustrating an incoming light transmitting section including two polarization filters, of which the angular difference between the transmission axes satisfies α=45 degrees.
Figure 10B:
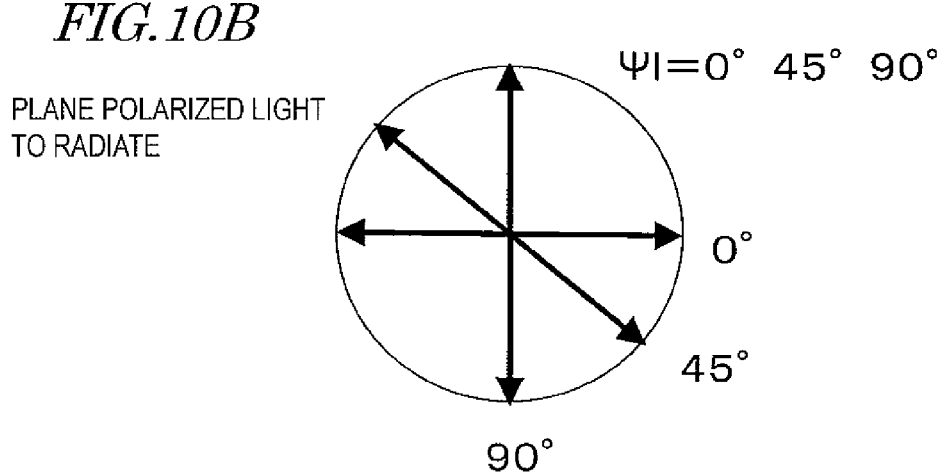
FIG. 10B shows the angles ψI defined by the planes of polarization of the polarized light source.

FIG. 10A illustrates an incoming light transmitting section in which the angle of the transmission axis of the polarization filter is set to be 0 degrees in the filter area L and 45 degrees in the filter area R, respectively. The angle of the transmission axis can also be defined in the same way as the angle ψI shown in FIG. 5. In this example, the difference α between the transmission axis angles of the left and right polarization filters is 45 degrees. FIG. 10B shows the angles of the planes of polarization of the illuminating light with which the object is illuminated. The angles shown in FIG. 10B correspond to the angles of the planes of polarization of the light rays that have returned from the object. It should be noted that the arrangement of the polarization filters shown in FIG. 10A is only an example. That is to say, the relations to be described below are also satisfied even if the angle of the transmission axis of the polarization filter in the filter area L is not set to be zero degrees.

Suppose the transmittance in a situation where the transmission axis of a polarization filter agrees with the axis of a plane polarized light ray incident on that polarization filter is Tp, which satisfies 0<Tp<1. Also, the ideal transmittance of the transparent area C is supposed to be one. Furthermore, the virtual intensities of the light rays transmitted through those areas L, R and C of the incoming light transmitting section 120 and then observed when the object is illuminated with a plane polarized light ray at an angle ψI are identified by $IFL\psi_I$, $IFR\psi_I$, and $IC\psi_I$, respectively. In that case, $IFL\psi_I$, $IFR\psi_I$, and $IC\psi_I$ are represented by the following Equations (2):

$$\begin{cases} IFL_{\psi_I} = T_P[\cos^2\psi_I]I_L \\ IFR_{\psi_I} = T_P[\cos^2(\psi_I - \alpha)]I_R \\ IC_{\psi_I} = I_C \end{cases} \quad (2)$$

The intensity $I\psi_I$ actually measured is the combined intensity of the three light rays that have been transmitted through the areas L, R and C of the incoming light transmitting section 120, and therefore, can be represented by the following Equation (3):

$$\begin{aligned} I_{\psi_I} &= IFL_{\psi_I} + IFR_{\psi_I} + IC_{\psi_I} \\ &= T_P[\cos^2\psi_I]I_L + T_P[\cos^2(\psi_I - \alpha)]I_R + I_C \\ &= \begin{bmatrix} T_P\cos^2\psi_I & T_P\cos^2(\psi_I - \alpha) & 1 \end{bmatrix} \begin{bmatrix} I_L \\ I_R \\ I_C \end{bmatrix} \end{aligned} \quad (3)$$

Figure 11:
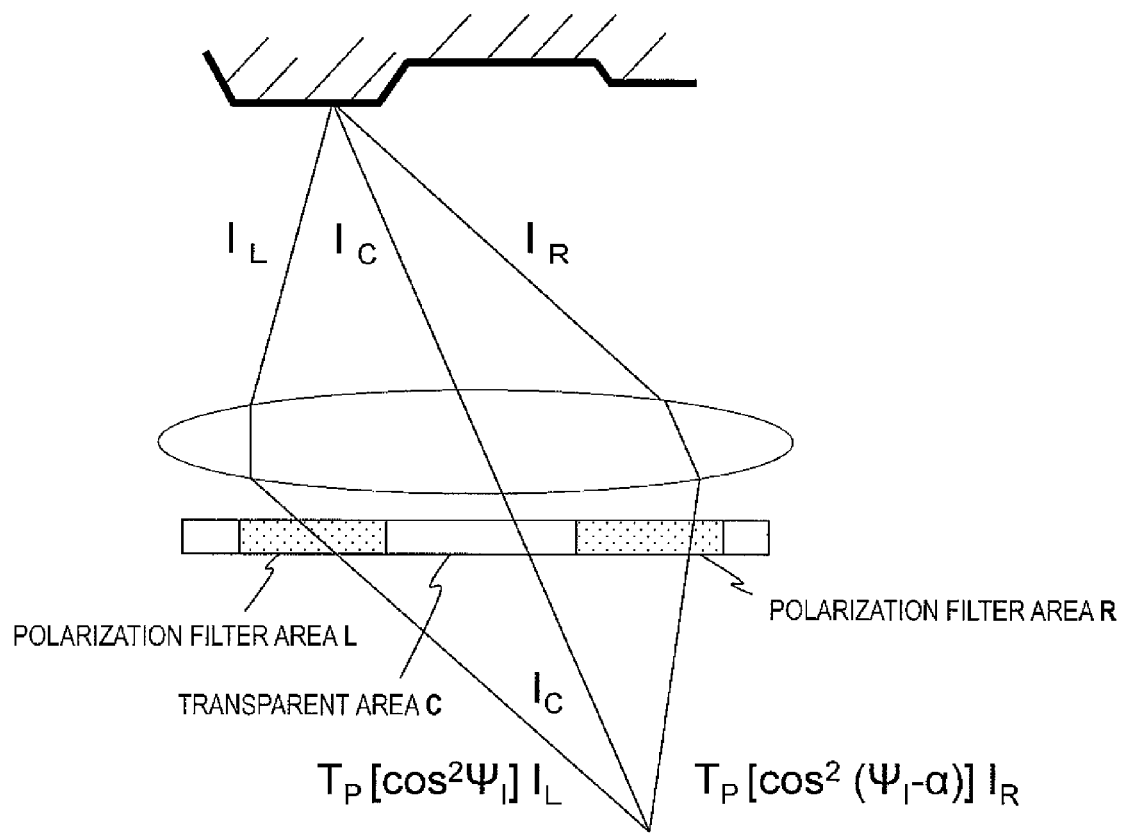
FIG. 11 illustrates light rays that are transmitted through respective areas of the incoming light transmitting section.

FIG. 11 schematically illustrates, with respect to a certain pixel, how the light that has returned from the object is transmitted through the areas L, C and R of the incoming light transmitting section 120. Due to the function of the lens, the light that has returned from the object is transmitted through the respective areas L, R and C and then converged toward, and combined at, a point on the image capturing plane.

For example, if three images of an object are captured by illuminating the object one after another with three plane polarized light rays that have mutually different polarization angles ψI of 0, 45 and 90 degrees, then the following simultaneous equations are obtained with respect to the intensity of each pixel:

$$\begin{cases} I_0 = T_P I_L + T_P I_R \cos^2\alpha + I_C \\ I_{45} = T_P \frac{1}{2} I_L + T_P I_R \cos^2\left(\frac{\pi}{4} - \alpha\right) + I_C \\ I_{90} = 0 + T_P I_R \cos^2\left(\frac{\pi}{2} - \alpha\right) + I_C \end{cases} \quad (4)$$

In Equations (4), $I_0$, $I_{45}$ and $I_{90}$ represent the intensities to be observed when ψI=0 degrees, when ψI=45 degrees, and when ψI=90 degrees, respectively. These intensities correspond to pixel signals to be obtained from respective pixels of the image sensor 110. This point will be described more generally. Supposing the three pixel signals generated by the image sensor when the polarized light source section illuminates the object with first, second and third plane polarized light rays, of which the respective planes of polarization define angles of $\theta_1$, $\theta_2$ and $\theta_3$ degrees with respect to a reference direction, are identified by $I\theta_1$, $I\theta_2$ and $I\theta_3$, respectively, the image processing section generates the plurality of images by performing arithmetic processing on those three pixel signals $I\theta_1$, $I\theta_2$ and $I\theta_3$ according to this embodiment.

If the Equations (4) are represented as a matrix, then the following Equation (5) can be obtained:

$$\begin{bmatrix} I_0 \\ I_{45} \\ I_{90} \end{bmatrix} = \begin{bmatrix} T_P & T_P\cos^2\alpha & 1 \\ \frac{T_P}{2} & T_P\cos^2(\frac{\pi}{4}-\alpha) & 1 \\ 0 & T_P\cos^2(\frac{\pi}{2}-\alpha) & 1 \end{bmatrix} \begin{bmatrix} I_L \\ I_R \\ I_C \end{bmatrix} = M \begin{bmatrix} I_L \\ I_R \\ I_C \end{bmatrix} \quad (5)$$

In this case, the determinant of the matrix M can be represented by the following Equation (6):

$$|M| = (T_P)^2 \begin{vmatrix} 1 & \cos^2\alpha & 1 \\ \frac{1}{2} & \cos^2(\frac{\pi}{4}-\alpha) & 1 \\ 0 & \cos^2(\frac{\pi}{2}-\alpha) & 1 \end{vmatrix}$$

$$= (T_P)^2 \cos\alpha\sin\alpha$$

$$= (T_P)^2 \frac{\sin 2\alpha}{2} \quad (6)$$

Consequently, if $\alpha$ falls within the range defined by the following Inequality (7), then $|M|$ becomes non-zero and therefore, its inverse matrix $M^{-1}$ should exist:

$$0 < \alpha < \frac{\pi}{2} \quad (7)$$
$$(0° < \alpha < 90°)$$

And if the inverse matrix $M^{-1}$ exists, intensities $I_L$, $I_R$ and $I_C$ can be calculated based on $I_0$, $I_{45}$ and $I_{90}$ by the following Equation (8):

$$\begin{bmatrix} I_L \\ I_R \\ I_C \end{bmatrix} = M^{-1} \begin{bmatrix} I_0 \\ I_{45} \\ I_{90} \end{bmatrix} \quad (8)$$

It should be noted that if $\alpha=90$ degrees, then the determinant of the matrix M would become equal to zero, and no solution could be obtained. This is because if an arbitrary combination of polarized light glancing angles consists of 0, $\psi 1$ and $\psi 2$, then Equation (6) will be:

$$|M| = (T_P)^2 \begin{vmatrix} 1 & 0 & 1 \\ \cos^2\psi_1 & \sin^2\psi_1 & 1 \\ \cos^2\psi_2 & \sin^2\psi_2 & 1 \end{vmatrix} = 0 \quad (9)$$

That is why $\alpha$ is an angle other than 90 degrees, which is a necessary condition according to the present disclosure. In this respect, the system of the present disclosure is quite different structurally from a lot of polarized light aided systems in which the polarization transmission axes of a pair of polarization filters are defined so as to cross each other at right angles.

In this example, the polarized light glancing angles used are supposed to be as many as unknown quantities. However, observation may also be made using more polarized light glancing angles and the simultaneous equations may also be solved by the minimum square method without using any inverse matrix. For example, the four angles of rotation of the polarized light of 0, 45, 90 and 135 degrees may also be used.

$$\begin{bmatrix} I_0 \\ I_{45} \\ I_{90} \\ I_{135} \end{bmatrix} = \begin{bmatrix} T_P & T_P\cos^2\alpha & 1 \\ \frac{T_P}{2} & T_P\cos^2(\frac{\pi}{4}-\alpha) & 1 \\ 0 & T_P\cos^2(\frac{\pi}{2}-\alpha) & 1 \\ \frac{T_P}{2} & T_P\cos^2(\frac{3\pi}{4}-\alpha) & 1 \end{bmatrix} \begin{bmatrix} I_L \\ I_R \\ I_C \end{bmatrix} = H \begin{bmatrix} I_L \\ I_R \\ I_C \end{bmatrix} \quad (10)$$

Since the determinant of the matrix M is non-zero according to Equation (6), the rank of M is three. That is why it can be concluded that the rank of a 4×3 matrix H, which is newly made by adding one row to M, should also be three. Consequently, if H and its transpose are multiplied together, the rank of the resultant 3×3 matrix should be three and its inverse matrix should exist. That is why the minimum square solution can be obtained by the following Equation (11):

$$\begin{bmatrix} I_L \\ I_R \\ I_C \end{bmatrix} = (H^tH)^{-1}H^t \begin{bmatrix} I_0 \\ I_{45} \\ I_{90} \\ I_{135} \end{bmatrix} \quad (11)$$

Figure 12:
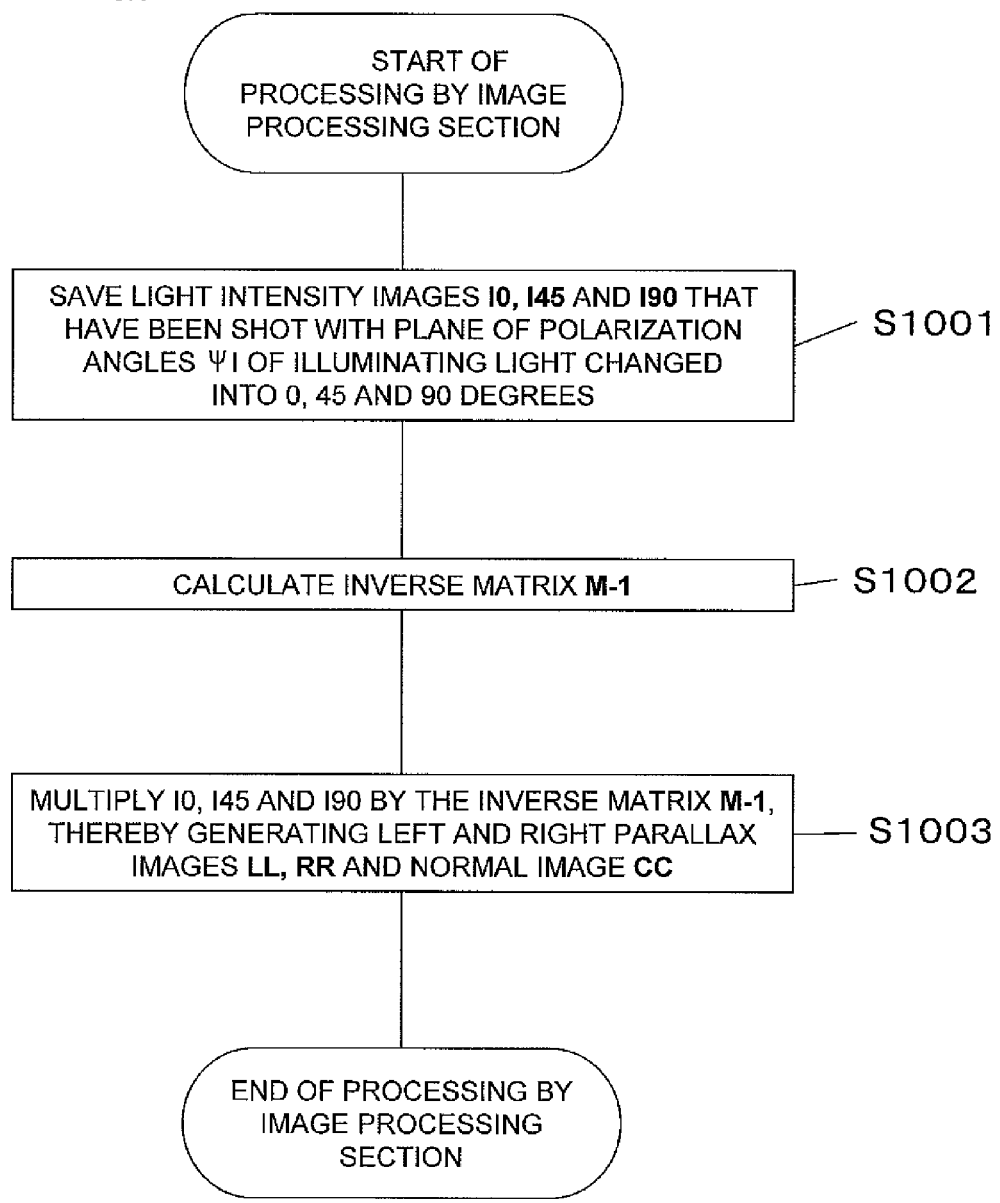
FIG. 12 is a flowchart showing the procedure of processing to be carried out by the image processor.

Hereinafter, it will be described with reference to FIG. 12 how the image processor 108 performs its image processing. FIG. 12 is a flowchart showing the procedure of the image processing to be carried out by the image processor 108.

First of all, in Step S1001, images are shot with the plane of polarization of the illuminating light rotated as described above. Next, in Step S1002, an inverse matrix is calculated. Then, in Step S1003, left and right multi-viewpoint images LL and RR and a normal image CC are generated based on those images. In this manner, according to the present disclosure, the multi-viewpoint images LL and RR can be generated just by performing a simple calculation on pixel values.

The display image processing section 121 converts the images LL and RR into an image to be displayed for 3D viewing. For example, the display image processing section 121 may display the LL and RR images alternately by switching them at very short intervals. In that case, the normal image CC may or may not be displayed.

Figure 13:
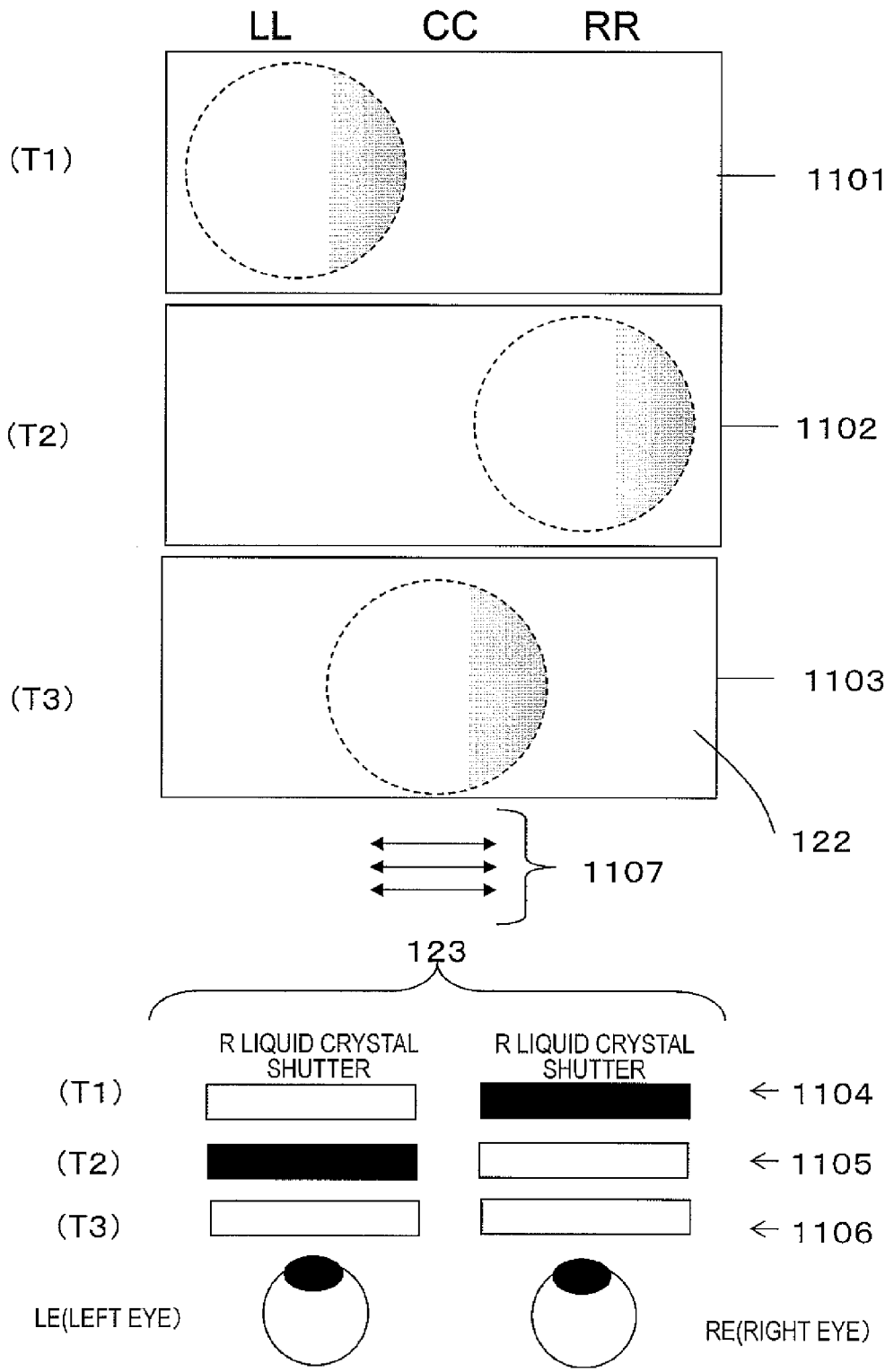
FIG. 13 illustrates how the images LL, RR and CC displayed on the display section and viewing glasses work.

FIG. 13 illustrates how the modes of observation may be changed appropriately between 3D viewing and normal viewing by alternately displaying the multi-viewpoint images LL and RR and the normal image CC on the display section. On the 3D display section 122, presented is only the LL image through a period T1 (which is a state 1101), only the RR image through the next period T2 (which is a state 1102), and only the CC image through the next period T3 (which is a state 1103). This video comes to the eye as either plane polarized light or circularly polarized light 1107 by being transmitted through a polarization filter plate, for example. The viewer observes the video by wearing a pair of viewing glasses 123, which may be liquid crystal shutters. The liquid crystal shutters of the viewing glasses are alternately opened (in light transmitting state) and closed (in light cutting state) with respect to the polarized light 1107 synchronously with the 3D display section 122. Specifically, through the period T1, the L liquid crystal shutter is opened but the R liquid crystal shutter is closed (which is a state 1104). Through the next period T2, the L liquid crystal shutter is closed but the R liquid crystal shutter is opened (which is a state 1105). And through the next period T3, the L and R liquid crystal shutters are both opened (which is a state 1106). By switching these two periods T1 and T2 at very short intervals, a 3D image is sensed to the human visual system.

Figure 14A:
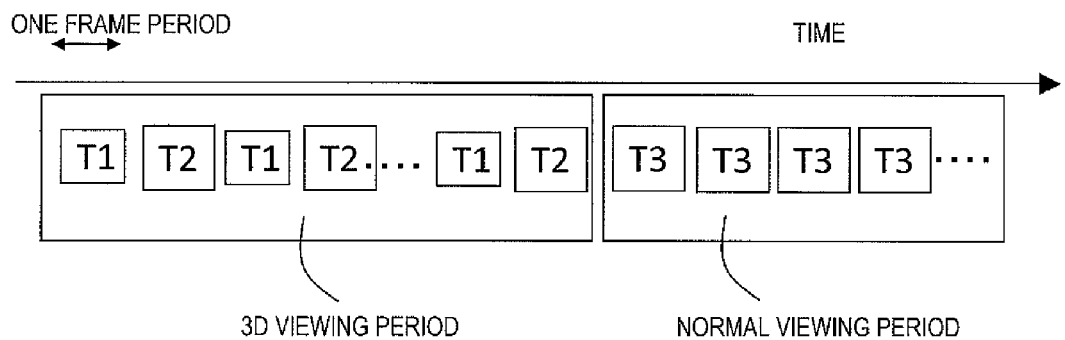
FIGS. 14A and 14B show 3D viewing and normal viewing periods according to an embodiment of the present invention.

FIGS. 14A and 14A show a combination of those three periods T1, T2 and T3 on the time axis. Specifically, FIG. 14A illustrates a situation where a 3D viewing period and a normal viewing period are switched with each other. When this technique is applied to an endoscope, an ordinary color image is observed during the normal viewing period. For example, overall screening is carried out on the internal wall of the stomach. In that case, as the camera and the light source are located at a long distance (of about 50 mm or more) from the stomach wall, the illuminating light needs to be used effectively and the stomach wall is observed using the bright CC image with high sensitivity. And once a diseased portion is spotted, the illuminating light needs to have its brightness increased sufficiently in order to approach that diseased portion (e.g., within 5 mm or less). As a result, even with an image that has been generated with decreased sensitivity based on the light rays that have been transmitted through the left and right polarization filter areas L and R with a small area, observation can be made easily enough. Consequently, the properties of normal viewing and 3D viewing can be both used effectively by changing the modes of observation into 3D viewing in that case in order to observe the local shape of the diseased portion closely. From the operational point of view, the periods T1 and T2 should alternate with each other through the 3D viewing period and only the period T3 should continue through the normal viewing period.

Figure 14B:
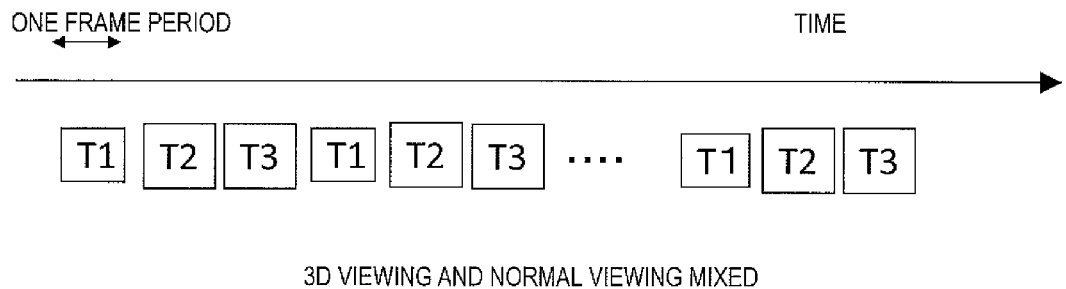

FIG. 14B shows a situation where 3D viewing and normal viewing modes are mixed. In this example, the periods T1, T2 and T3 recur alternately one after another. In that case, as the quantity of light decreases and the sensitivity declines during the 3D viewing period, the periods T1 and T2 may be somewhat longer than the period T3.

Optionally, the display image processing section 121 may further perform additional processing. For example, the image CC is not an image with parallax but may have a portion that is similar to the multi-viewpoint images. That is why as to such a similar portion, multi-viewpoint images LL and RR with high sensitivity may be generated by adding the image CC to the multi-viewpoint images.

By performing these processing steps, the shape of the surface of an organ wall can be viewed as a 3D image with an endoscope. As a result, according to this embodiment, difficulty in observing surface shape, which is one of the problems with an endoscope, can be overcome.

In the embodiment described above, the number of polarization filter areas is supposed to be two. However, according to the present disclosure, the number of polarization filter areas may also be three or more. Furthermore, those polarization filters do not have to be horizontally shifted from each other. Rather, the multi-viewpoint images can also be obtained even if those polarization filters are shifted vertically and/or obliquely. As long as such multi-viewpoint images are obtained, either three-dimensional information or a parallax image representing the 3D shape of the object's surface can also be obtained.

Embodiment 2

Hereinafter, a second embodiment of the present disclosure will be described.

In the 3D image shooting apparatus of this embodiment, the illuminating light is not plane polarized light, which is a major difference from its counterpart of the first embodiment described above.

FIG. 15 schematically illustrates an overall arrangement for a 3D image shooting apparatus according to this embodiment. In this embodiment, the white non-polarized light that has been emitted from the light source 104 is guided through the light guide 105 and then irradiates the object as it is (i.e., as non-polarized light). That is to say, the tip portion 113 does not have to include the plane of polarization control element 106 of the first embodiment and the controller 102 does not have to include the synchronizer 112, either.

In this embodiment, the light that has been reflected from the object does not turn into plane polarized light until it is transmitted through the polarization filter areas R and L of the incoming light transmitting section 120. According to this embodiment, instead of getting the illuminating light polarized, a mosaic array of polarization filters with multiple different polarization transmission axis directions is arranged on the image capturing plane of the image sensor 114.

Figure 16A:
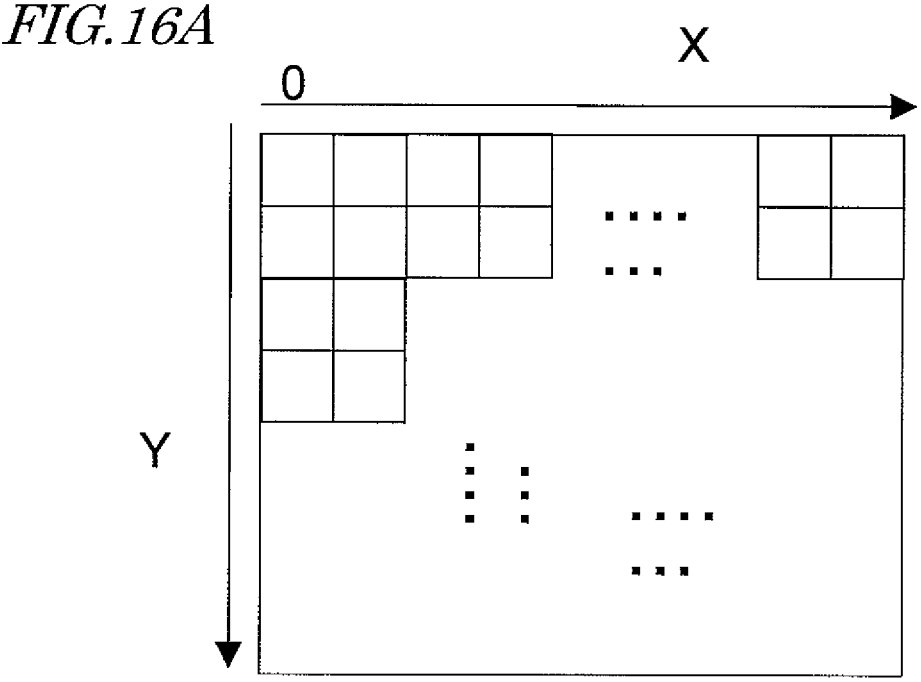
FIGS. 16A and 16B illustrate another exemplary arrangement of photosensitive cells in an image sensor.
Figure 16B:
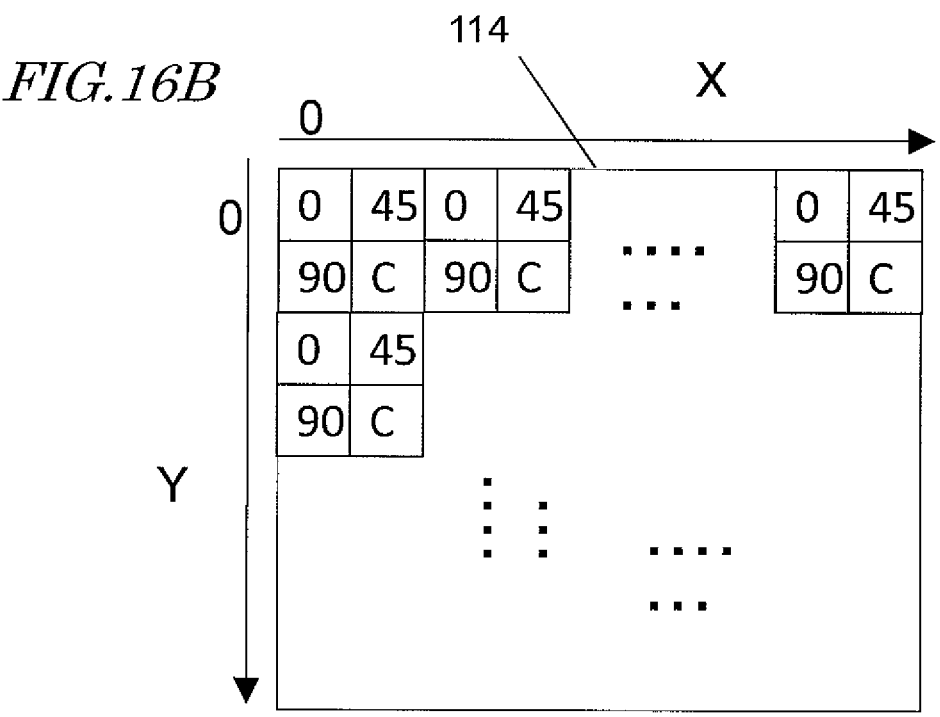

FIGS. 16A and 16B illustrate an exemplary arrangement for the image capturing plane of the image sensor 114 of this embodiment. As shown in FIG. 16B, an array of polarization filters that have multiple different polarization transmission axis directions is arranged instead of the color mosaic filter. Each of these photosensitive cells generates, by photoelectric conversion, an electrical signal representing the quantity of the light received through its associated polarization filter. In FIG. 16B, "0", "45" and "90" denote polarization filters which are arranged so that their polarization transmission axis directions define angles of 0, 45 and 90 degrees, respectively, with respect to a reference direction, while "C" denotes a transparent area.

Setting three or more different polarization transmission axis directions for polarization filters to be provided for the image sensor 114 is equivalent to rotating the plane of polarization of illuminating light to three or more different angles. In other words, the angle of polarization $\psi I$ of the illuminating light of the first embodiment corresponds to the polarization transmission axis direction of a polarization filter to be provided for the image sensor 114. That is why as the value of the angle of polarization $\psi I$ in each of the equations mentioned for the first embodiment, the angle defined by the polarization transmission axis of the polarization filter of the image sensor 114 may be given.

Thus, according to this embodiment, there is no need to use the plane polarized light as illuminating light or to rotate the plane of polarization of the illuminating light, either. As a result, according to this embodiment, surface information required can be obtained easily even for a moving picture, which is certainly advantageous. Nevertheless, since a polarization filter array needs to be provided for the image sensor 114, it becomes difficult to use a color mosaic filter. That is why this embodiment can be used particularly effectively when a monochrome image is going to be captured.

Embodiment 3

Hereinafter, a third embodiment of the present disclosure will be described.

In the 3D image shooting apparatus of this embodiment, the polarization filter areas are arranged differently in the incoming light transmitting section 120, which is a major difference from its counterpart of the first embodiment described above.

Figure 17:
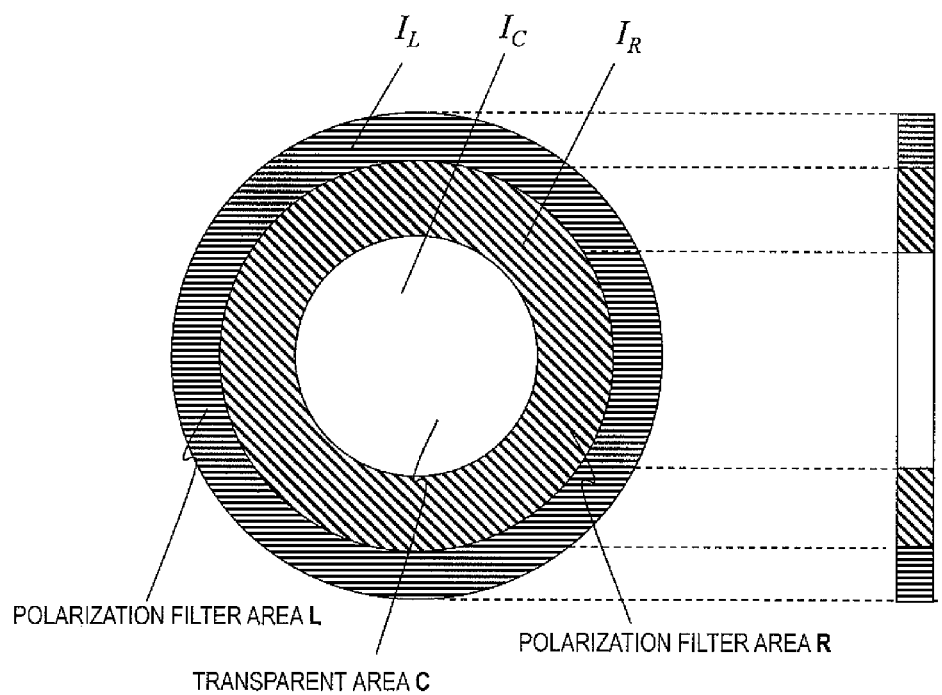
FIG. 17(a) is a plan view of the incoming light transmitting section 120 as viewed from the image sensor 110 and FIG. 17(b) is a cross-sectional view thereof.

FIG. 17 illustrates the incoming light transmitting section 120 of this embodiment. Specifically, portion (a) of FIG. 17 is a plan view of the incoming light transmitting section 120 as viewed from the image sensor 110, while portion (b) of FIG. 17 illustrates a cross section of the incoming light transmitting section 120. As shown in portion (a) of FIG. 17, the incoming light transmitting section 120 is comprised of an optically transparent area C and concentric polarization filter areas L and R, each of which has a polarization filter. These polarization filter areas L and R each have a concentric ring shape and surround the transparent area C concentrically. The center of the concentric ring polarization filter areas (L, R) agrees with the center of the transparent area C.

A certain angular difference $\alpha$ (where $0<\alpha<90$ degrees) is defined between the respective transmission axes of the polarization filters that are provided for the filter areas L and R.

Figure 18:
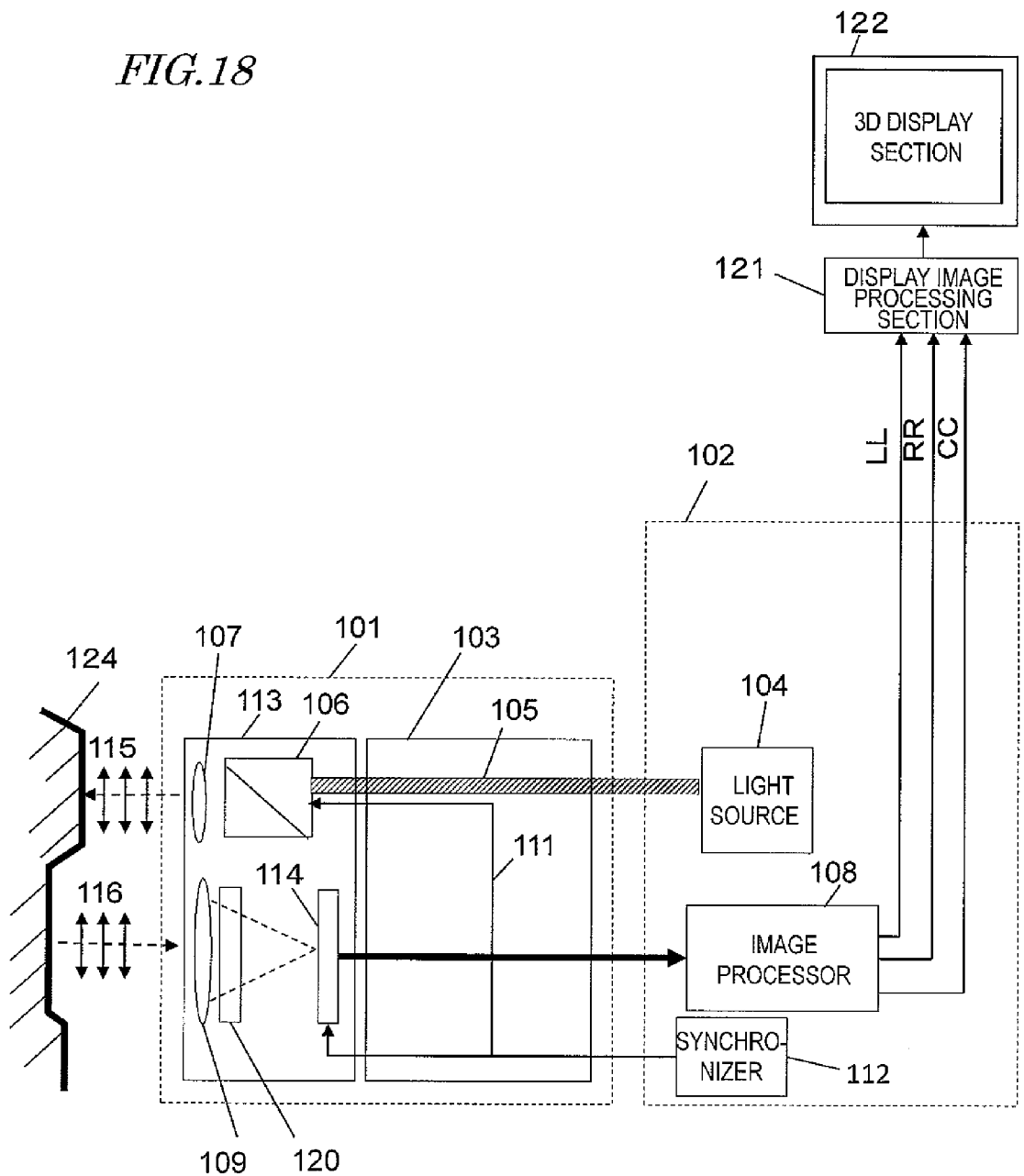
FIG. 18 illustrates a configuration for a 3D image shooting apparatus as a third embodiment of the present invention.

FIG. 18 schematically illustrates an overall configuration for a 3D image shooting apparatus according to this embodiment. The apparatus of this embodiment has quite the same configuration as its counterpart of the first embodiment except the structure of the incoming light transmitting section 120. Thus, what has already been described for the first embodiment will not be stated all over again to avoid redundancies. According to this embodiment, the viewer does not have to wear any pair of viewing glasses 123, nor does he or she in the fourth and fifth embodiments to be described below.

Figure 19A:
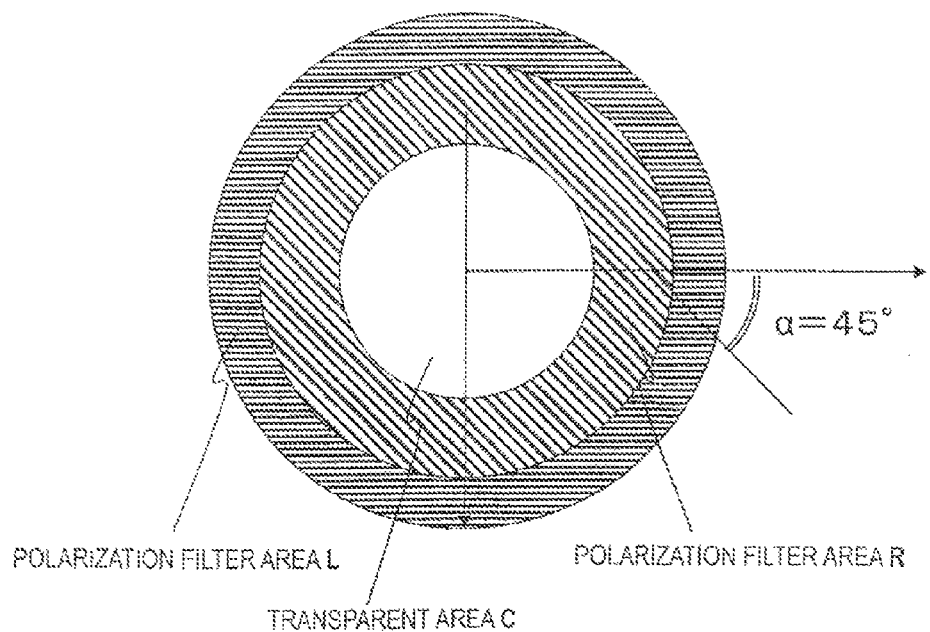
FIG. 19A is a plan view illustrating an incoming light transmitting section including two polarization filters, of which the angular difference between the transmission axes satisfies α=45 degrees, according to the third embodiment
Figure 19B:
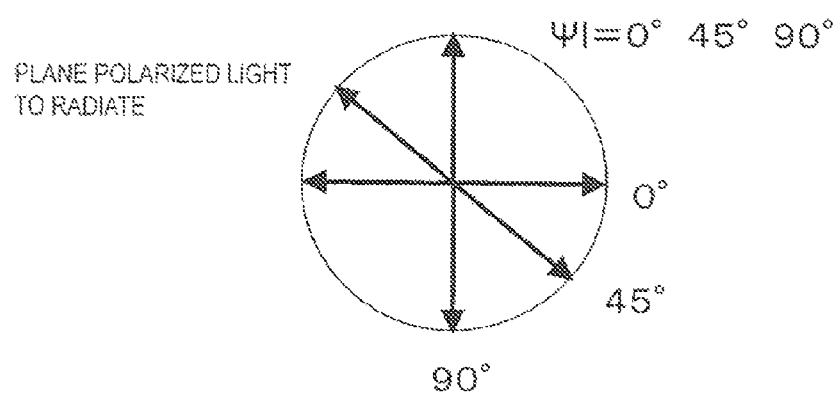
FIG. 19B shows the angles ψI defined by the planes of polarization of the polarized light source.

FIG. 19A illustrates an incoming light transmitting section in which the angle of the transmission axis of the polarization filter is set to be 0 degrees in the filter area L and 45 degrees in the filter area R, respectively. The angle of the transmission axis can also be defined in the same way as the angle $\psi$I shown in FIG. 5. In this example, the difference $\alpha$ between the transmission axis angles of the left and right polarization filters is 45 degrees. FIG. 19B shows the angles of the planes of polarization of the illuminating light with which the object is illuminated. The angles shown in FIG. 19B correspond to the angles of the planes of polarization of the light rays that have returned from the object. It should be noted that the arrangement of the polarization filters shown in FIG. 19B is only an example. That is to say, the angle of the transmission axis of the polarization filter in the filter area L does not have to be set to be zero degrees.

According to this embodiment, the incoming light transmitting section 120 has concentric polarization filter areas L and R, and therefore, multi-viewpoint images with parallax in the horizontal direction such as the ones described for the first and second embodiments cannot be obtained. However, according to this embodiment, an image produced by light that passes through a portion of the shooting lens 109 that is close to its outer edge and an image produced by light that passes through another portion of the shooting lens 109 that is relatively close to center of the shooting lens 109 can be obtained at the same time. And if image processing is carried out by using Equation (8) or (11) that has already been described for the first embodiment, the intensities $I_L$, $I_R$ and $I_C$ can be obtained based on $I_0$, $I_{45}$ and $I_{90}$. The intensities $I_L$, $I_R$ and $I_C$ according to this embodiment are the intensities of the light rays that have been respectively transmitted through the polarization filter areas L and R and the transparent area C of the incoming light transmitting section 120.

By using these intensities $I_L$, $I_R$ and $I_C$ thus obtained, multiple images associated with different lens aperture sizes can be obtained. That is to say, according to this embodiment, an image produced by light rays that have been transmitted through the transparent area C and the inner polarization filter area R of the incoming light transmitting section 120 and an image produced by light rays that have been transmitted through the transparent area C and the inner and outer polarization filter areas R and L are obtained by performing image processing on pixel signals.

It is known that a blur kernel, which is a point spread function defining the defocus blur (that is an image blur caused by defocusing), will depend on the lens aperture size. That is why by using multiple different lens aperture sizes, the distance from the focal plane to the object's surface (i.e., information about the depth of the object's surface) can be obtained from each of the multiple images. And once such depth information is obtained, an image can be generated with the position of the focal plane set arbitrarily. If the position of the focal plane changes, a blurry image is obtained due to defocusing involved. However, an image representing a part of the object's surface on the focal plane does not get blurred but an image representing another part of the object's surface that is located rather distant from the focal plane gets blurred significantly. If such images are displayed on the display section with the focal plane changed, the object can be perceived three-dimensionally. Such a technique for obtaining information about the depth of the object's surface by performing image processing on a plurality of images using multiple different lens aperture sizes is disclosed in Paul Green et al.: "Multi-Aperture Photography", ACM Transactions on Graphics, Vol. 26, No. 3, Article 68, July 2007, for example.

Embodiment 4

Hereinafter, a fourth embodiment of the present disclosure will be described.

In the 3D image shooting apparatus of this embodiment, the illuminating light is not plane polarized light, which is a major difference from its counterpart of the third embodiment described above.

FIG. 20 schematically illustrates an overall arrangement for a 3D image shooting apparatus according to this embodiment. In this embodiment, the white non-polarized light that has been emitted from the light source 104 is guided through the light guide 105 and then irradiates the object as it is (i.e., as non-polarized light). That is to say, the tip portion 113 does not have to include the plane of polarization control element 106 of the first embodiment and the controller 102 does not have to include the synchronizer 112, either.

In this embodiment, the light that has been reflected from the object does not turn into plane polarized light until it is transmitted through the polarization filter areas R and L of the incoming light transmitting section 120. According to this embodiment, instead of getting the illuminating light polarized, a mosaic array of polarization filters with multiple different polarization transmission axis directions is arranged on the image capturing plane of the image sensor 114.

The image capturing plane of the image sensor 114 of this embodiment may have the same arrangement as what is shown in FIGS. 16A and 16B. According to this embodiment, there is no need to use the plane polarized light as illuminating light or to rotate the plane of polarization of the illuminating light, either, as in the second embodiment. As a result, according to this embodiment, surface information required can be obtained easily even for a moving picture, which is certainly advantageous. Nevertheless, since a polarization filter array needs to be provided for the image sensor 114, it becomes difficult to use a color mosaic filter. That is why this embodiment can be used particularly effectively when a monochrome image is going to be captured.

Embodiment 5

Figure 21A:
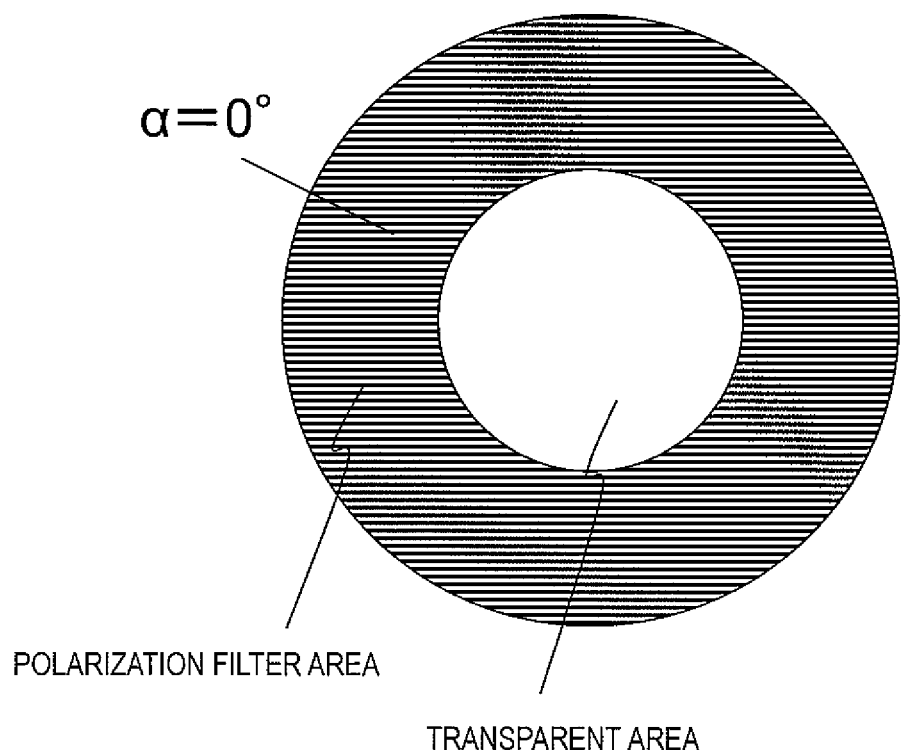
FIG. 21A is a plan view illustrating the structure of an incoming light transmitting section according to a fifth embodiment of the present invention and FIG. 21B shows the angles ψI defined by the planes of polarization of a polarized light source.
Figure 21B:
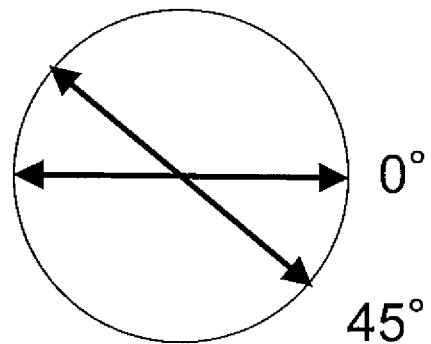

Next, a fifth embodiment of the present disclosure will be described with reference to FIGS. 21A and 21B. FIG. 21A is a plan view illustrating an incoming light transmitting section 120 according to this embodiment. The 3D image shooting apparatus of this embodiment is different from the basic configuration shown in FIG. 1 only in the incoming light transmitting section 120. Specifically, in the incoming light transmitting section 120 of this embodiment, a transparent area CL is arranged at the center and only one polarization filter area R is arranged concentrically outside of it. As shown in FIG. 21B, two images may be captured by setting the angles of the planes of polarization of the incoming polarized light to be 0 and 45 degrees. If the intensities of the light rays that have been transmitted through the transparent area and the polarization filter area are identified by ICL and IR, respectively, and if the intensities observed at the illuminating light polarization angles of 0 and 45 degrees are identified by $I_0$ and $I_{45}$, respectively, the following Equation (12) is satisfied as in the first embodiment described above:

$$\begin{bmatrix} I_0 \\ I_{45} \end{bmatrix} = \begin{bmatrix} T_P\cos^2 0 & 1 \\ T_P\cos^2(\frac{\pi}{4}) & 1 \end{bmatrix} \begin{bmatrix} I_L \\ I_{CL} \end{bmatrix} \quad (12)$$

$$= T_P A \begin{bmatrix} I_R \\ I_{CL} \end{bmatrix}$$

$$= T_P \begin{bmatrix} 1 & 1 \\ \frac{1}{2} & 1 \end{bmatrix} \begin{bmatrix} I_R \\ I_{CL} \end{bmatrix}$$

By solving this Equation (12), the following Equation (13) is obtained:

$$\begin{bmatrix} I_R \\ I_{CL} \end{bmatrix} = T_P \begin{bmatrix} 2 & -2 \\ -1 & 2 \end{bmatrix} \begin{bmatrix} I_0 \\ I_{45} \end{bmatrix} \quad (13)$$

In this embodiment, the illuminating light may have different polarization rotation angle. The determinant of the matrix A is given by the following Equation (14):

$$|A| = 1 - \cos^2\psi \neq 0 \quad (14)$$

Therefore, ψ may be 0 and 90 degrees, for example.

According to this embodiment, the light that has passed through the lens is just split into two rays using the incoming light transmitting section 120, and therefore, the arrangement can be simplified, which is advantageous. According to this embodiment, multiple images associated with different lens aperture sizes can also be obtained.

As described above, according to embodiments of the present disclosure, the incoming light transmitting section 120 has no opaque portions, and therefore, bright multi-viewpoint images or images associated with multiple different lens aperture sizes can be obtained even though a single-vision system is used.

On top of that, the light that has been transmitted through the polarization filter area and the light that has been transmitted through the transparent area can be separated from each other through arithmetic processing. Thus, a normal color image or a monochrome image can also be observed in the same way as in a known image capturing system that uses an ordinary lens. For that reason, unlike the pertinent art, two image capturing optical systems are never needed. That is to say, the endoscope of this embodiment can obtain both a parallax image for 3D viewing and a normal light intensity image at a time in a single mode of operation, which is a distinct advantage.

As described above, a 3D image shooting apparatus according to an embodiment of the present disclosure can obtain multi-viewpoint images by performing arithmetic processing on multiple images that have been shot with the plane of polarization rotated. That is why no opaque portions are needed anymore and the quantity of incoming light is never wasted in vain. According to an embodiment of the present disclosure, just by performing arithmetic processing between images, images that have low sensitivity but do have parallax and color images that have no parallax but do have good enough sensitivity can be obtained with no time lag.

The present disclosure is broadly applicable to the field of image processing that needs observing, checking, or recognizing the object's surface shape using a medical endoscope, a medical camera for dermatologists, dentists, internists or surgeons, an industrial endoscope, a fingerprint scanner, or an optical surface analyzer.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. A 3D image shooting apparatus comprising:
    a polarized light source section that sequentially illuminates an object with three or more kinds of plane polarized light rays, of which the planes of polarization define mutually different angles;
    an image capturing section that sequentially captures an image of the object that is being illuminated with each of the plane polarized light rays; and
    an image processing section,
    wherein the image capturing section includes:
    a lens that produces an image of light that has returned from the object that is being illuminated by the polarized light source section;
    an image sensor that generates, through photoelectric conversion, a pixel signal based on the image produced by the lens; and
    an incoming light transmitting section which transmits the light that has returned from the object and which has a transparent area and a plurality of polarization filter areas, and
    wherein the plurality of polarization filter areas are arranged outside of the transparent area, generally have a concentric ring shape, and include left and right filter areas that are respectively arranged on the left- and right-hand sides of the optical axis of the lens so that their polarization transmission axis directions define an angle α that is greater than zero degrees but smaller than 90 degrees, and wherein based on the pixel signal that is generated by the image sensor when the object is being illuminated with each of the plane polarized light rays, the image processing section generates a plurality of images from light that has been transmitted through the transparent area and light that has been transmitted through the plurality of polarization filter areas.

2. The 3D image shooting apparatus of claim 1, wherein the polarized light source section gets non-polarized light transmitted through a plane of polarization changer, thereby radiating plane polarized light rays, of which the plane of polarization sequentially changes into one of two or more different ones after another.

3. The 3D image shooting apparatus of claim 1, wherein based on the pixel signal that is generated when the object is being illuminated with each of the three or more kinds of plane polarized light rays, of which the planes of polarization define mutually different angles, the image processing section generates a left-hand-side image from light that has been transmitted through the left filter area of the incoming light transmitting section and a right-hand-side image from light that has been transmitted through the right filter area of the incoming light transmitting section.

4. The 3D image shooting apparatus of claim 1, wherein if the three pixel signals generated by the image sensor when the polarized light source section illuminates the object with first, second and third plane polarized light rays, of which the respective planes of polarization define angles of $\theta_1$, $\theta_2$ and $\theta_3$ degrees with respect to a reference direction, are identified by $I\theta_1$, $I\theta_2$ and $I\theta_3$, respectively, the image processing section generates the plurality of images by performing arithmetic processing on those three pixel signals $I\theta_1$, $I\theta_2$ and $I\theta_3$.

5. The 3D image shooting apparatus of claim 1, wherein the image capturing section includes, as the image sensor, either a monochrome image sensor or a color image sensor.

6. An endoscope comprising:
a polarized light source section that sequentially illuminates an object with three or more kinds of plane polarized light rays, of which the planes of polarization define mutually different angles; and
an image capturing section that sequentially captures an image of the object that is being illuminated with each of the plane polarized light rays,
wherein the image capturing section includes:
a lens that produces an image of light that has returned from the object that is being illuminated by the polarized light source section;
an image sensor that generates, through photoelectric conversion, a pixel signal based on the image produced by the lens; and
an incoming light transmitting section which transmits the light that has returned from the object and which has a transparent area and a plurality of polarization filter areas, and
wherein the plurality of polarization filter areas are arranged outside of the transparent area, generally have a concentric ring shape, and include left and right filter areas that are respectively arranged on the left- and right-hand sides of the optical axis of the lens so that their polarization transmission axis directions define an angle .alpha. that is greater than zero degrees but smaller than 90 degrees.

* * * * *